US 7,399,310 B2

(12) United States Patent
Edoga et al.

(10) Patent No.: US 7,399,310 B2
(45) Date of Patent: *Jul. 15, 2008

(54) ENDOVASCULAR STAPLER

(75) Inventors: John K. Edoga, Morristown, NJ (US); Thierry Richard, Florham Park, NJ (US)

(73) Assignee: Edrich Vascular Devices, Inc., Morristown, NJ (US)

( * ) Notice: Subject to any disclaimer, the term of this patent is extended or adjusted under 35 U.S.C. 154(b) by 398 days.

This patent is subject to a terminal disclaimer.

(21) Appl. No.: 10/737,466

(22) Filed: Dec. 16, 2003

(65) Prior Publication Data

US 2004/0176663 A1 Sep. 9, 2004

Related U.S. Application Data

(60) Provisional application No. 60/501,060, filed on Sep. 8, 2003, provisional application No. 60/433,692, filed on Dec. 16, 2002.

(51) Int. Cl.
*A61B 17/115* (2006.01)
*A61B 17/068* (2006.01)

(52) U.S. Cl. ............... 606/219; 606/142; 606/151; 227/175.1; 227/177.1

(58) Field of Classification Search ......... 606/139–144, 606/148, 151, 153, 219, 157–158, 213, 219; 227/175.1–175.4, 176.1, 19, 182.1, 177.1; 411/445, 451.2, 439, 442
See application file for complete search history.

(56) References Cited

U.S. PATENT DOCUMENTS

| 3,561,429 | A |   | 2/1971  | Jewett        |         |
|-----------|---|---|---------|---------------|---------|
| 3,735,762 | A | * | 5/1973  | Bryan et al.  | 606/143 |
| 3,765,762 | A |   | 10/1973 | LiDonnici     |         |
| 4,196,836 | A | * | 4/1980  | Becht         | 227/110 |
| 4,425,915 | A | * | 1/1984  | Ivanov        | 606/143 |
| 4,595,007 | A | * | 6/1986  | Mericle       | 606/221 |
| 4,669,469 | A |   | 6/1987  | Gifford, III et al. |   |
| 5,158,564 | A |   | 10/1992 | Schnepp-Pesch et al. | |
| 5,246,156 | A |   | 9/1993  | Rothfuss et al. |       |
| 5,346,115 | A |   | 9/1994  | Perouse et al. |        |
| 5,370,651 | A |   | 12/1994 | Summers       |         |
| 5,392,978 | A | * | 2/1995  | Velez et al.  | 227/177.1 |

(Continued)

FOREIGN PATENT DOCUMENTS

FR    2 746 292 A1    9/1997

*Primary Examiner*—Glenn K. Dawson
*Assistant Examiner*—Kathleen Sonnett
(74) *Attorney, Agent, or Firm*—Lerner, David, Littenberg, Krumholz & Mentlik, LLP

(57) ABSTRACT

An endovascular stapler for securing an endograft to a vessel is disclosed. The stapler includes a staple housing adapted for storing at least one staple therein. The staple housing having an exit area for discharge of the at least one staple therethrough. The stapler also includes an actuating assembly adapted for discharging the at least one staple through the exit area and a displacement mechanism in operative association with the staple housing near the exit area. The displacement member is operative for pushing the exit area against the endograft when discharging the at least one staple therethrough. The displacement mechanism may comprise a balloon adapted to be inflated and deflated positioned near the exit area. The unbent staples may be shaped as elongate W shapes, or may alternatively be straight wire segments. The staples may be bent upon discharge.

3 Claims, 19 Drawing Sheets

U.S. PATENT DOCUMENTS

| | | |
|---|---|---|
| 5,431,323 A | 7/1995 | Smith et al. |
| 5,630,540 A * | 5/1997 | Blewett .................... 227/176.1 |
| 5,695,504 A * | 12/1997 | Gifford et al. ................ 606/153 |
| 5,720,755 A | 2/1998 | Dakov |
| 5,728,047 A | 3/1998 | Edoga |
| 5,908,395 A | 6/1999 | Stalker et al. |
| 6,149,660 A * | 11/2000 | Laufer et al. ................ 606/143 |
| 6,171,330 B1 * | 1/2001 | Benchetrit ................... 606/219 |
| 6,592,593 B1 | 7/2003 | Parodi et al. |
| 6,830,174 B2 * | 12/2004 | Hillstead et al. .......... 227/175.1 |
| 2002/0004663 A1 | 1/2002 | Gittings et al. |
| 2003/0149441 A1 | 8/2003 | Shifrin et al. |
| 2004/0176663 A1 | 9/2004 | Edoga et al. |
| 2005/0004582 A1 * | 1/2005 | Edoga et al. ................ 606/139 |

* cited by examiner

SECTION A/A'

SECTION B/B'

SECTION C/C'

SECTION D/D'

ENDOVASCULAR STAPLER

CROSS REFERENCE TO RELATED APPLICATIONS

The present provisional application relates to U.S. Provisional Patent Application Ser. No. 60/433,692 filed Dec. 16, 2002, and U.S. Provisional Application No. 60/501,060 filed Sep. 8, 2003, the disclosures of which are hereby incorporated herein by reference.

BACKGROUND OF THE INVENTION

The present invention relates to a stapling device for use in the fixation of endovascular grafts to the walls of vessels. Fixation of grafts utilizing the present invention may be conducted during initial implantation. However, the present invention may also be utilized to arrest the vexing complication of proximal or distal migrations following the prior implantation of such grafts.

It is well known that endovascular grafts may be inserted into the human body during numerous medical procedures. Grafts are typically inserted into vessels and held in place by friction, such as with self-expanding or balloon expandable stents. The grafts may also be affixed to vessels with hooks or barbs.

The grafts may be formed from synthetic materials, such as polyester, expanded polytetraflouroethylene ("ePTFE"), or others. The grafts may also be formed of natural vessels harvested from other areas of the body or from a donor mammal. Notwithstanding the various materials utilized, migration of the grafts over time remains a problem.

Caudad device migration is known to lead to a Type 1 endoleak with aneurysm sac reperfusion, enlargement and rupture. Cephalad device migration may lead to coverage of the renal artery orifices and renal insufficiency.

Such device migration is caused by many factors. One known factor is poor patient selection. Patients with cone shaped aortic necks, severe neck tortuosity, short necks or who have a laminated thrombus present at the landing site are generally susceptible to device migration problems. Other device migration issues are caused by changing aortic morphology following device implantation. Finally, migration may be caused by device structural fatigue and device design related issues. Even absent these conditions, device migration has been found.

Treatment of caudad migrations have traditionally been conducted by the addition of "sleeves" to the proximal end of the graft in an effort to regain purchase between the graft and the vessel it is attached to in order to maintain a seal between the two. More drastic options include resorting to conventional surgery. These late conversions are, unfortunately, associated with a high mortality rate.

Treatment options for the cephalad migrations are even less attractive. In the face of continued migration, resignation may be the only option as such migration may lead to renal insufficiency requiring hemodialysis. To permit device removal, a typical conversion in this case involves supraceliac aortic cross-clamping, and its associated problems.

Prior attempts at fixation of migrating devices, including additions of hooks, barbs, tackers, and other fastening devices have proven to be insufficient or impractical. It would therefore be advantageous to provide an endovascular stapling device which may be used to adequately arrest existing migrations, as well as secure new grafts in a manner likely to eliminate future migration. Actual fixation of the graft to the aortic neck at multiple points will also prevent the aorta itself from enlarging.

SUMMARY OF THE INVENTION

The endovascular stapler of the present invention is designed to overcome the deficiencies of the prior art. In one embodiment, the endovascular stapler may comprise a staple housing adapted for storing at least one staple therein, the staple housing may have an exit area for discharge of the at least one staple therethrough, an actuating assembly adapted for discharging the at least one staple through the exit area, and a displacement mechanism in operative association with the staple housing near the exit area, the displacement member operative for pushing the exit area against the endograft when discharging the at least one staple therethrough. The displacement mechanism may comprise a balloon positioned near the exit area. The balloon may be adapted to be selectively inflated and deflated. The balloon may also be noncompliant. The staple may be deformed prior to exiting the exit area. The stapler may also be adapted for use with a staple having an elongated W shape. In addition, the actuating assembly may comprise a pusher and a trigger, the pusher adapted to be advanced by the trigger to discharge the at least one staple.

In another embodiment, the endovascular stapler for securing an endograft to a vessel may comprise a trigger housing comprising a trigger mechanism within the housing; a staple housing having a proximal end and a distal end, the staple housing coupled at the proximal end of the staple housing to the trigger housing, the staple housing adapted to store a staple, the staple housing having a staple exit area formed therein near the distal end thereof; and, a balloon exterior to the staple housing near the distal end thereof, the balloon adapted to be selectively inflated and deflated to push the staple exit area against the endograft. The trigger mechanism may be actuated to drive a staple from the staple housing through the staple exit area into the endograft and the vessel. The endovascular stapler may further comprise an output boss penetrating the trigger housing; a guide wire exit port near the distal end of the staple housing; a guide wire channel extending from the guide wire exit port to the output boss; and, a guide wire extending within the guide wire channel. The staple housing may be guided to a particular location within the vessel by sliding the staple housing along the guide wire. The trigger assembly may further comprise a pusher operatively engaged with a trigger, the pusher extending from within the trigger housing to the staple exit area, wherein the pusher is adapted to advance through the staple housing to push the staple from the staple exit area. The endovascular stapler may further comprise an actuator having an inclined surface, wherein the pusher further comprises an inclined surface adjacent to the inclined surface of the actuator, advancement of the pusher in an advancement direction through the staple housing bringing the inclined surface of the pusher into contact with the inclined surface of the actuator to shift the actuator in a direction substantially perpendicular to the advancement direction of the pusher. The shifting of the actuator may drive a staple through the staple exit area. The stapler may further comprise a staple détente associated with the staple exit area, the staple détente adapted to deform the staple prior to exiting the staple exit area. The pusher may further comprise a ramped surface on a side of the pusher, the ramped surface adapted to rotate the staple détente away from the staple exit area during advancement of the pusher.

In yet another embodiment, the endovascular stapler for securing an endograft to a vessel may comprise a trigger housing comprising a trigger mechanism; a staple housing having a proximal end at the trigger housing and a distal end remote from the trigger housing, the staple housing comprising a staple channel adapted to store a plurality of staples in tandem, the staple channel extending from the proximal end of the staple housing to a staple exit area near the distal end of the staple housing; and, a pusher extending into the staple channel from within the trigger housing; wherein the pusher is adapted to advance through the staple channel upon actuation of the trigger mechanism to advance the plurality of staples stored in tandem in the staple channel such that a first staple may be discharged through the staple exit area. The staple channel may comprise a curved portion adjacent the staple exit area, the curved portion configured to shape the staples as they are discharged from the staple exit area. The stapler may further comprise a balloon inflation port penetrating the trigger housing; a balloon inflation channel extending within the staple housing and in fluid communication with the balloon inflation port; and, a balloon exterior to the staple housing and in fluid communication with the balloon inflation channel; wherein the balloon may be selectively inflated and deflated to push the staple exit area against the endograft. The balloon may be positioned opposite to the staple exit area. The stapler may further comprise an output boss penetrating the trigger housing; a guide wire exit port near the distal end of the staple housing; a guide wire channel extending within the staple housing from the output boss to the guide wire exit port; and, a guide wire extending within the guide wire channel; wherein the staple housing may be guided to a vessel by sliding the staple housing along the guide wire.

In yet another embodiment, the stapler for stapling a vessel may comprise a trigger housing having an internal cavity; a trigger mechanism extending from within the internal cavity of the trigger housing; an elongate staple housing extending from the trigger housing to a staple exit area formed in the elongate staple housing, the elongate staple housing adapted to store at least one staple; a pusher having a leading portion within the staple housing and a trailing portion within the internal cavity of the trigger housing, the pusher having an inclined surface at its leading end; an actuator having an inclined surface disposed adjacent to the inclined surface of the pusher; and, a staple détente mounted within the staple housing between the actuator and the staple exit area; wherein actuation of the trigger advances the leading portion of the pusher such that the inclined surface of the pusher interacts with the inclined surface of the actuator to force the actuator toward the staple exit area thereby deforming the at least one staple by engagement with the staple détente prior to discharging the at least one staple from the staple exit area. The at least one staple stored in the staple housing may be formed in the shape of an elongated W prior to being discharged from the staple exit area.

In yet another embodiment, the endovascular stapler for connecting a stent graft to a vessel may comprise a trigger housing having an elongate staple housing extending therefrom, the elongate staple housing having a staple exit area adapted to be inserted into a vessel, the elongate staple housing adapted to store a staple; a pusher extending within the staple housing from the trigger housing; a trigger mechanism within the housing, the trigger mechanism adapted to advance the pusher within the staple housing to push a staple stored in the elongate staple housing through the staple exit area to connect the stent graft to the vessel; and, a balloon adjacent the staple housing, the balloon inflatable to force the staple exit area against the stent graft. The stapler may further comprise a staple détente mounted within the staple housing, the staple détente adapted to shape the staple prior to exiting the staple exit area. The staple may be formed in the shape of an elongated W prior to being discharged from the staple exit area.

In one method of repairing an endograft in a vessel with an endovascular stapler having a distal end and a balloon associated therewith, the method may comprise inserting the distal end of the endovascular stapler into the endograft; inflating the balloon so as to push the distal end of the endovascular stapler against the endograft; discharging a staple from the endovascular stapler into the endograft.

In a further method of repairing an endograft in a vessel with an endovascular stapler having a distal end forming a staple exit area, a trigger for deploying staples, and a balloon near the staple exit area, the method may comprise inserting the distal end of the endovascular stapler into the endograft; inflating the balloon to push the staple exit area against the endograft; and, deploying a staple from the staple exit area into the endograft and the vessel. The method may further comprise partially deflating the balloon; rotating the endovascular stapler; reinflating the balloon so as to push the stapler exit area against the endograft in a location adjacent to the first staple; and, deploying a second staple from the staple exit area into the endograft and the vessel.

A still further method of performing surgery on a vessel having an endograft therein may comprise providing a plurality of staplers, each stapler having a stapler housing storing a staple and a balloon capable of being inflated and deflated; inserting the stapler housing of the first of said plurality of staplers into said endograft; inflating the balloon of said first of said plurality of staplers so as to push the stapler housing against the endograft; and, advancing the first staple from within the stapler housing such that the first staple pierces the endograft and the vessel wall. The method may further comprise deflating the balloon; removing the stapler housing of said first of said plurality of staplers from said endograft; inserting the second of said plurality of stapler housings into said endograft; inflating the balloon so as to push the second of said plurality of stapler housings against the endograft area other than at the location of the first staple; advancing the staple of the second of said plurality of staplers from within the stapler housing such that the second staple pierces the endograft in an area other than at the location of the first staple.

In accordance with another aspect of the invention, an endovascular stapler for securing an endograft to a vessel may comprise a staple housing adapted for storing a plurality of staples therein, the staple housing having a plurality of exit areas for discharge of the plurality of staples therethrough; an actuating assembly adapted for discharging the plurality of staples through the plurality of exit areas, the actuating assembly comprising a plurality of staple pushers adapted to advance the plurality of staples through the plurality of exit areas and a trigger adapted to advance the plurality of staple pushers; and, a displacement mechanism in operative association with the staple housing near the exit areas, the displacement member operative for pushing the exit areas against the endograft when discharging the plurality of staples therethrough. The plurality of staples may be arranged radially about a longitudinal centerline of the staple housing. Alternatively, the plurality of staples may be arranged linerally within said staple housing.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

In regard to the drawings.

DETAILED DESCRIPTION

Figure 1:
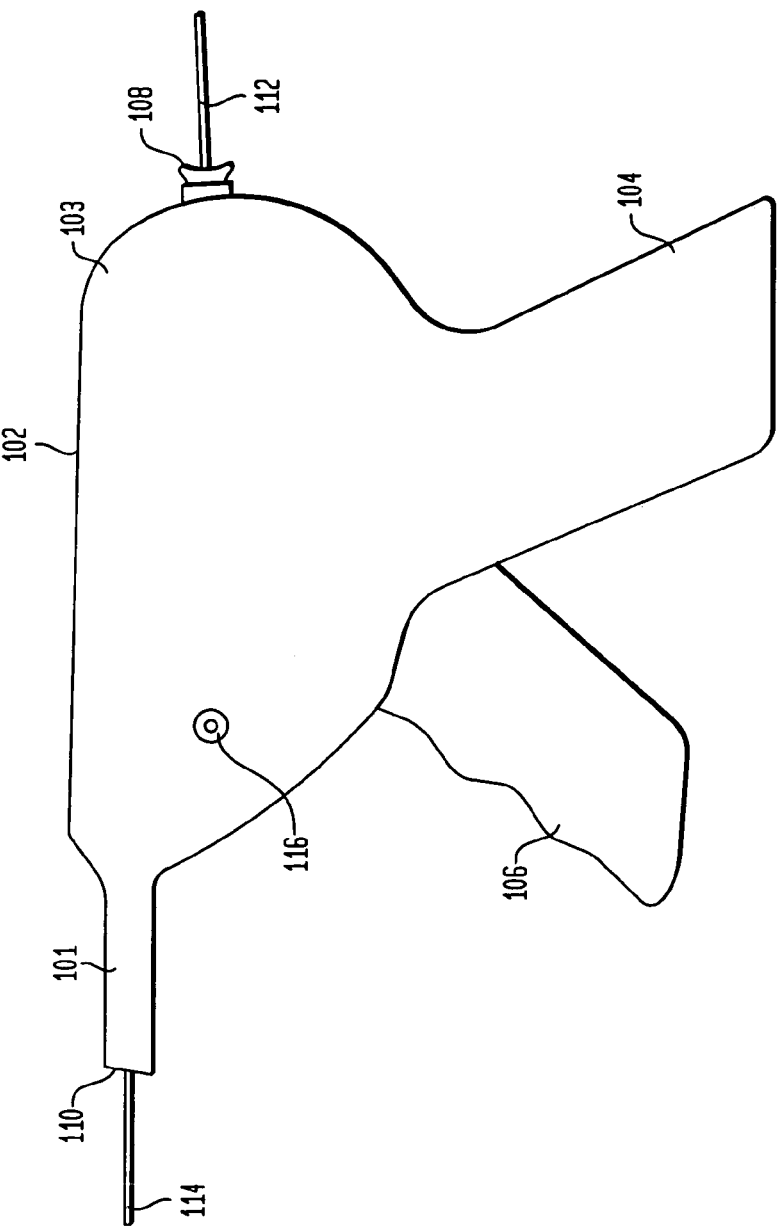
FIG. 1 is plan view of the handle portion of a stapler in accordance with one embodiment of the present invention.

In the following is described the preferred embodiments of the endovascular stapler of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

In general, the endovascular stapler is a device which includes a stapling portion, or staple housing, intended to be inserted into the human body of a patient through an artery and apposed against a vessel wall, such as an aortic wall, or a graft. In order to maintain this position, a displacement device, such as a balloon, may be inflated near the stapling portion to push the stapling portion against the aortic wall or graft. Preferably, the displacement device is a noncompliant balloon. However, compliant balloons may also be utilized. Other displacement devices comprising webbed elements or multiple rods may also be utilized. A staple may then be advanced through the aortic wall and graft by actuating a trigger located on the body of the endovascular stapler, which remains outside of the patient's body. The staple may be either preformed with the some initial curvature or it may be flat. Either way, the stapling portion typically includes a conforming element to curve the staple as it advances. The staple will then penetrate the aortic wall and the graft and will curve in a predictable path such that its leading edge loops back, possibly repenetrating the exterior of the aortic wall and graft, thus holding the aortic wall and the graft against each other.

In embodiments where multiple staples may be inserted, the noncompliant balloon may be deflated and the stapler may be rotated to a second position, wherein another staple may be driven. The process may be repeated numerous times over the full 360° until a sufficient number of staples have been driven to adequately secure the graft to the aortic wall. Typically, this will entail driving up to eight staples.

In embodiments where the endovascular stapler houses only a single staple, the central portion of the stapler may be removed, reloaded and reinserted numerous times in order to drive multiple staples. Alternatively, several pre-loaded staplers may be provided. After discharging the staple from the first stapler, the stapler may be removed and discarded, wherein a second stapler may be inserted. This process may be repeated until a sufficient number of staples have been driven. Thus, the surgical staff will generally be ready with up to eight pre-loaded staplers per procedure, each stapler being utilized successively.

The endovascular stapler of the present invention may be an "over the wire" device designed to fit through a typical sheath for aortic and iliac arterial use, such as a 10 French sheath. It is also possible that the stapler may be miniaturized to fit through smaller sheaths for fixation of endografts in smaller caliber vessels.

In some embodiments, the stapler fires multiple staples sequentially. In such cases, the staples may consist of special precuts of alloy, such as Phynox, with sufficient column strength to be stacked in tandem within the staple channel and to be sequentially pushed therethrough. The staples must also be sufficiently pliable to easily track the curved internal staple guide, for some embodiments of the invention. In other embodiments, the staples must be loaded individually. In still further embodiments, the staples may be loaded automatically from a cartridge, but are not stacked in tandem. Rather, they may reside side-by-side in the cartridge.

The stapler is generally introduced through a groin sheath or other suitable access into the lumen of an endograft. Its leading elements are advanced to the proximal end of the endograft which should be accurately identified. Such identification may be by utilizing an ultrasonic probe. For future endografts, the ends of the graft fabric may be boldly marked with radio opaque thread. For older devices, radiologic techniques such as road mapping may be used to locate the ends of the graft. As is known in the art, multiple guide wires may be used during surgery.

When the stapling portion of the stapler is aligned with the proximal end of the endograft, the stapler head may be forcibly abutted against the endograft and vessel wall by inflation of a preferably noncompliant balloon. In this position, a single stroke of the stapler trigger preferably causes forward displacement of the staple pusher sufficient to advance a single staple through the graft and vessel wall.

In some embodiments, the curve of the staple guide causes the staple to form a circle or spiral, with a single piercing point on the leading portion of the staple. In other embodiments, the staple may form an exaggerated W. In this case, each end of the staple will pierce the endograft and the vessel wall as the staple is deformed by a staple détente.

In the case of an automatically loading stapler with staples aligned in tandem, the trigger of the stapler handle is then ratcheted back and cocked for the next firing. The specialized ratcheted design of this pusher and trigger is such that when fully cocked, a single trigger pull causes exactly the pusher excursion required to deploy the lead staple fully and bring the trailing staple segment into position at the tip of the curved staple guide for the firing of the next staple. For single staple designs, the stapler may be retracted and reloaded prior to the firing of a second staple. Alternately, additional staplers may be utilized during a single procedure, each firing only a single staple. Where multiple staples are fired from a cartridge holding staples side-by-side, the ratcheting mechanism of the trigger may include a feature permitting the pusher to be withdrawn back toward the body of the stapler, such that it is positioned for the firing of subsequent staples after the firing of a previous staple.

Inflation and deflation of the preferably noncompliant balloon may be performed manually or with any of the many available devices used for inflation and deflation of angioplasty balloons. A liquid such as dilute contrast or saline may also be used to distend the balloon.

Following each staple deployment, the balloon may be partially deflated, the stapler rotated, and the process repeated to deploy the next staple. For embodiments where staples are aligned in tandem, one limiting factor to the number of staples per device, and thus the length of the device, is the column strength of the staple alloy as the staples aligned in a row are each driven by the trailing staples, and ultimately by the excursion of the staple pusher. It will be readily apparent that the staples should be of sufficient column strength so as not to become deformed within the stapler prior to being applied. It will also be apparent that a single staple may be required to push several proceeding staples.

In embodiments where the staples are stored in tandem, the staples may be cut such that the diamond shaped tip of each trailing staple fits into a diamond shaped cavity formed at the end of each leading staple. For devices employing a single staple or employing a cartridge of side-by-side staples, the column strength of the individual staple is less of a concern. Of course, it should be sufficient to adequately secure the stent graft, however.

Referring to the figures, FIG. 1 depicts an endovascular stapler 100 in accordance with one embodiment of the present invention. As is shown, the stapler 100 may generally be shaped like a gun. The stapler 100 may comprise a housing 102 having a handle 104 and a trigger 106 extending therefrom. The housing may also include a barrel 101 having an output aperture 110. An input boss 108 may be located at the rear 103 of the housing 102. A guide wire 112 may extend into the input boss. Extending from the output aperture 110 may be a staple housing 114. The stapler 100 may also include a balloon inflation port 116.

Figure 2:
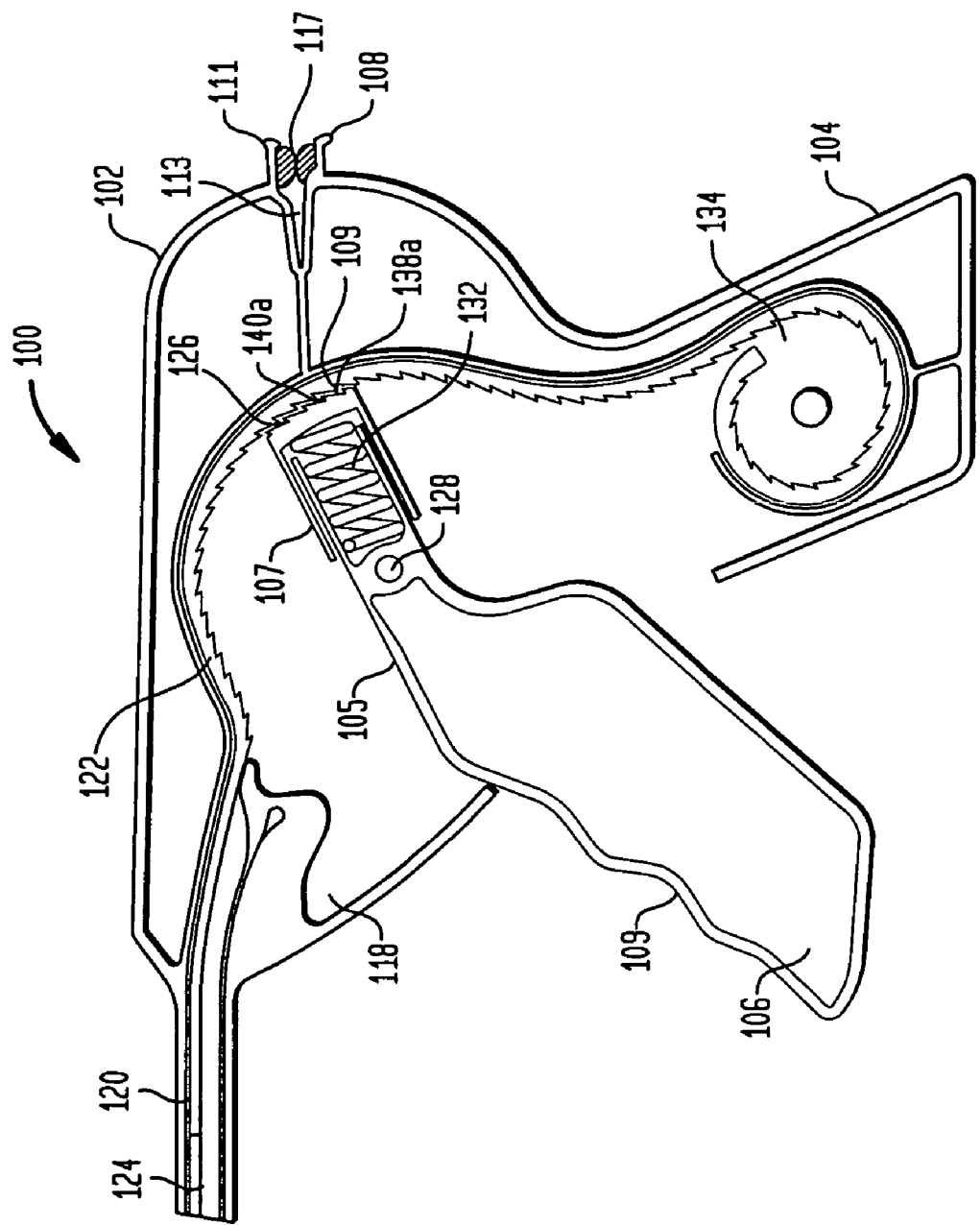
FIG. 2 is a sectional view of the stapler of FIG. 1 showing the internal components thereof.

FIG. 2 depicts a cut-away view of the stapler 100 of FIG. 1. As shown, the trigger 106 may comprise an inner section 105 and an outer section 107. The inner section 15 may also include a grip 109, exterior to the housing 102. The inner section 105 may include a pin 128 attaching the trigger 106 to the housing 102, and about which the trigger may rotate. The trigger 106 may also include a spring mechanism (not shown) to bias the trigger 106 away from the handle 104. The outer section 107 of the trigger 106 may be attached to the inner section by a spring 132. Advantageously, the outer section 107 is permitted to shift relative to the inner section 105, to compress the spring 132. A toothed element 126 of the outer section 107 includes teeth 109 having sloped sections 138 and edges, or lips 140. Each of the sloped sections 138 of the teeth 109 assist with ratcheting action of the trigger 106, as will be discussed hereinafter.

A ratcheted stapler pusher 120 may curve between the trigger 106 and a path created by the internal cavity 118 formed from the housing 102. The pusher 120 may include a ratcheted portion 122 at its trailing portion and a cylindrical portion 124 at its leading portion. The ratcheted portion 122 includes sloped sections 138 which may engage the toothed elements 126 of the stapler trigger 106. Upon actuation of the stapler trigger 106, which initiates rotation of the toothed elements 126 about pin 128, the pusher 120 may be displaced through the barrel 101 toward the distal end 130 (FIG. 4) of the stapler 100. As the trigger 106 is returned to its initial position, spring 132 permits ratcheting of the toothed elements 126 such that the pusher 120 remains in this advanced position. Portions of the ratcheted portion 122 of the pusher 120 may be stored in a spiral configuration within staging area 134, located within the handle 104 of the stapler 100.

Also shown in FIG. 2 are the internal components of the input boss 108. The input boss 108 comprises a flange 111 formed from the housing 102. The flange includes a cavity 113 extending into the internal cavity 118 of the housing 102. Within the cavity 113 near the flange 111 may be a pair of rubberized elements 115 having a boundary 117 therebetween. The guide wire 112 (FIG. 1) may be permitted to pass along this boundary from the exterior of the housing 102 to the internal cavity 118. Once inside the internal cavity 118, the guide wire may be permitted to extend through the barrel 101 into the guide wire channel 144 (FIG. 4) of the staple housing 114, as will be discussed.

Figure 3:
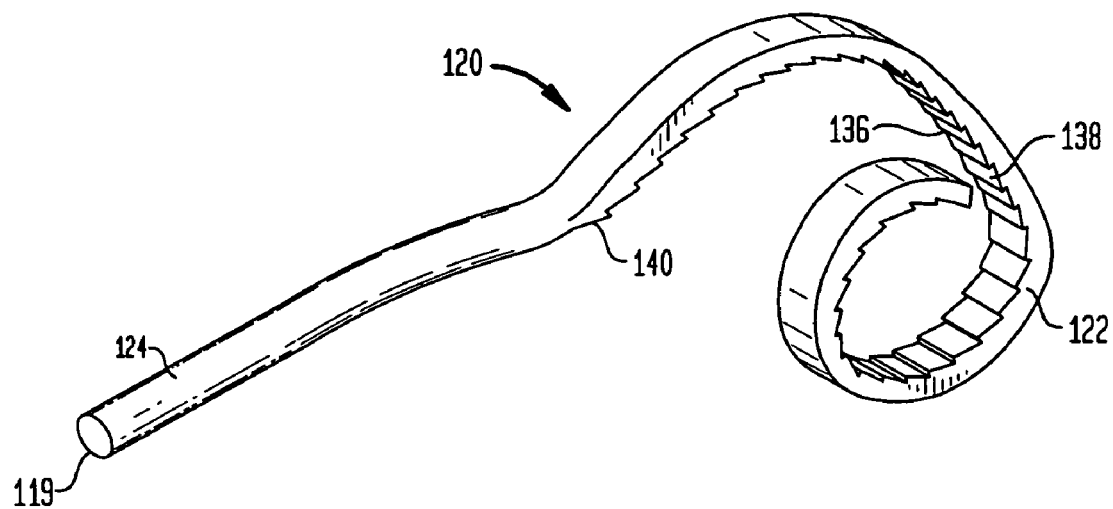
FIG. 3 is a perspective view of a pusher forming a portion of the stapler of FIG. 1.

FIG. 3 depicts a perspective view of the pusher 120. This figure clearly depicts the cylindrical portion 124 at the front of the pusher 120 and the ratcheted portion 122 at the rear of the pusher. The ratcheted portion 122 may comprise a series of ramps 136 having sloped sections 138 ending in lips 140. As discussed, the toothed element 126 of the stapler trigger 106 incorporates teeth 109 which may be sized and configured similarly to the sloped sections 138. The engagement of each of these elements facilitates displacement of the pusher 120 when the trigger 106 is activated, but permits ratcheting of the trigger upon the return stroke.

Also shown in FIG. 3 is the front face 119 of pusher 120. As will be discussed, the front face 119 of the pusher may be adapted to contact and advance a series of staples 148 (FIG. 4).

Figure 4:
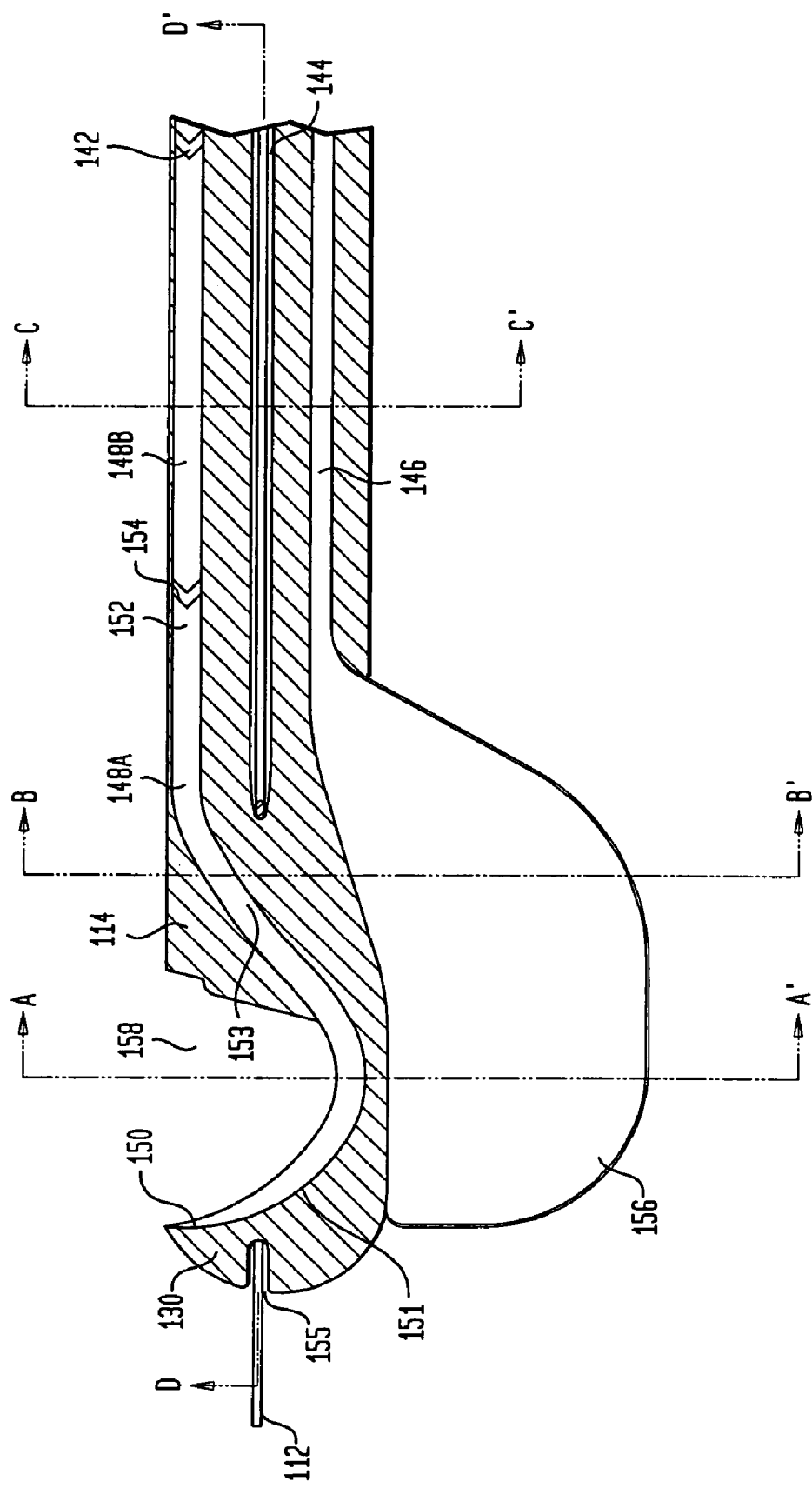
FIG. 4 is a longitudinal sectional view of the distal end of the staple housing forming a portion of the stapler of FIG. 1 showing the internal components thereof.

FIG. 4 depicts a longitudinal sectional view of the distal end 130 of the staple housing 114. As shown, the staple housing 114 may incorporate a staple channel 142, a guide wire channel 144, and a balloon inflation channel 146. Each of the channels may be generally cylindrical and typically run the entire length of the staple housing 114 from the outlet aperture 110 of the housing 102 to the distal end 130 of the staple channel 146.

The staple channel 142 typically houses a series of staples 148 placed consecutively in tandem including a first staple 148a and a second staple 148b. Preferably, each staple has a pointed proximal end 150 and a distal end 152 with a cavity 154 or recess matching the pointed proximal end. The cavity of the leading staple, such as the first staple 148a, therefore may be filled by the pointed proximal end 150 of the subsequent staple, such as the second staple 148b.

As will be discussed, the stapler 100 is generally employed to fire a multiplicity of staples 148 sequentially to secure a graft to a vessel. The staples 148 preferably consist of special precuts of alloy, such as Phynox, with sufficient column strength to be placed in tandem within the staple channel 142 so as to be pushed ahead by the trailing staples. Each of the staples 148 is also preferably sufficiently pliable to easily track the curved internal staple guide 151.

For example, the first staple 148a may be pushed by the second staple 148b, as well as the subsequent staples, by the pusher 120 upon actuation of the trigger 106. As the first staple travels along the staple channel 142, it will begin to be bent by a bending portion 153 of the staple channel 142, toward the distal end 130 of the staple housing 114. It will be appreciated that the bending portion 153 of the staple housing curves such that the staple 148 exiting the bending portion will be pre-curved as it enters the internal staple guide 151. As will be discussed hereinafter, as the staple 148 passes the staple guide 151, it will continue to be shaped such that the staple will form a loop capable of penetrating each of a graft and a vessel in at least two locations.

The guide wire channel 144 extends along the entire length of the staple housing 114 parallel and adjacent to the staple channel 142. The guide wire channel provides a housing for the guide wire 112, which is used to advance the distal end 130 of the stapler 100 to the location where the stapling is to be conducted.

Generally, advancement of the endovascular stapler 100 is considered to be via an "over the wire" type system. As an "over the wire" device, the staple housing 114 portion of the stapler 100 is designed to be guided through vessels following the path of a previously installed guide wire 112. For example, a guide wire 112 may be placed in an artery in a surgical procedure. The distal end 130 of the staple housing 114 may then be pushed along the length of the guide wire 112, which travels from a guide wire exit point 155 at the distal end 130, through the guide wire channel 144 and out the input boss 108 of the housing 102. Once the distal end 130 reaches its destination, advancement may cease and the stapler 100 is ready deploy a staple 148. It will be appreciated that the staple housing 114 may be constructed of flexible materials such that it may bend as necessary along the path toward the area in which a staple 148 is to be deployed.

Preferably, the endovascular stapler of the present invention is designed to fit through a 10 French sheath for aortic and iliac arterial use. However, it is also foreseeable that the stapler may be miniaturized to fit through smaller sheaths for fixation of endografts in smaller caliber vessels.

Also shown in FIG. 4 is the balloon inflation channel 146 of the staple housing 114. Extending from the balloon inflation channel 146 is a noncompliant balloon 156. In the view shown in FIG. 4, it will be appreciated that the noncompliant balloon 156 is shown inflated. In a deflated condition, the noncompliant balloon is generally quite thin, and typically fits neatly against the balloon inflation channel 146.

The noncompliant balloon 156 may be inflated prior to the firing of a staple 148. One purpose of inflating the noncompliant balloon 156 is to force the staple exit area 158 of the staple housing 114 against the area where the staple 148 is to be fired. This not only places the staple 148 immediately adjacent to the receiving area, but it assists with preventing the staple housing 114 from being moved, linearly or rotationally, during the firing of the staple 148.

Selective inflation and deflation of the noncompliant balloon 156 is completed through the balloon inflation port 116 of the housing 102. It will be appreciated that the balloon inflation port 116 may include a valve (not shown) upon which a liquid source (not shown) may be attached. The liquid source may be permitted to flow into the balloon inflation port 116 to inflate the noncompliant balloon 156. Deflation of the noncompliant balloon 156 may be accomplished at the balloon inflation port 116 by releasing liquid therefrom, such as by opening the valve or by sucking liquid out of the noncompliant balloon 156 through use of the liquid source, which may have the capability of reversing direction of flow to form a vacuum. It will be appreciated that the balloon inflation port 116 is in fluid communication with the noncompliant balloon 156 via the balloon inflation channel 146. Inflation and deflation may also be conducted with any of the available devices used for inflation and deflation of angioplasty balloons. Typically, the liquid used for inflating and deflating the balloon will be dilute contrast or saline.

Upon firing of the staple 148, the noncompliant balloon 156 may then be deflated so the staple housing 114 may be rotated to a second position in preparation for the firing of a second staple 148. Prior to firing the second staple 148, the noncompliant balloon 156 may be re-inflated to place the staple exit area 158 of the stapler 100 in position in preparation for firing.

Figure 5:
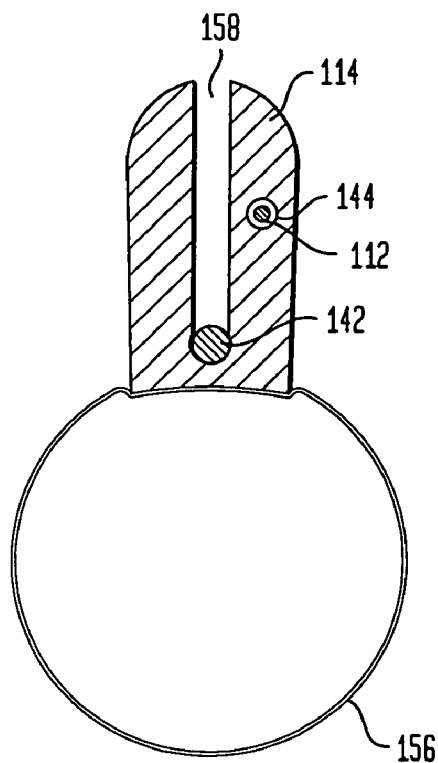
FIG. 5 is a cross-sectional view of the distal end of the staple housing shown in FIG. 4 taken along section lines A-A.

FIG. 5 depicts a cross sectional view of the staple housing 114 taken along section line A-A of FIG. 4. As with FIG. 4, the noncompliant balloon 156 is shown inflated. As shown in FIG. 5, the guide wire channel 144 may be offset within the staple housing 114 around the staple exit area 158 (also shown in FIG. 4). This offset allows for the formation of the curved area 153 of the staple channel 142, as well as the staple guide 151 along the longitudinal centerline of the staple housing 114.

Figure 6:
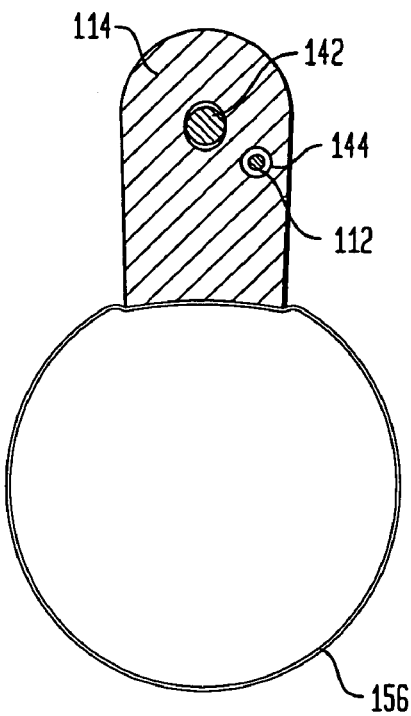
FIG. 6 is a cross-sectional view of the distal end of the staple housing shown in FIG. 4 taken along section lines B-B.

FIG. 6 depicts a cross sectional view of the staple housing 114 taken along section line B-B of FIG. 4. As shown in FIG. 4, section line B-B is taken closer to the housing 102 than section line A-A. In this cross-section, the staple exit area 158 is not yet visible. Yet, a staple 148 within the staple channel 142 and the guide wire 112 within the guide wire channel 144 clearly are. In addition, the noncompliant balloon 156 is shown in the inflated condition.

Figure 7:
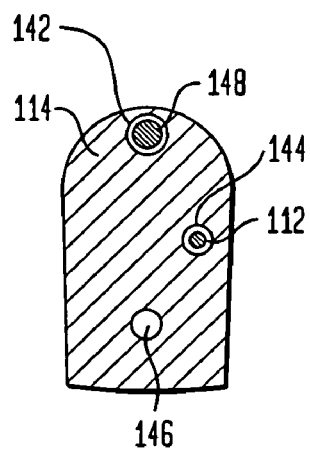
FIG. 7 is a cross-sectional view of the distal end of the staple housing shown in FIG. 4 taken along section lines C-C.

FIG. 7 depicts a cross sectional view of the staple housing 114 taken along section line C-C of FIG. 4. In this upstream section, it is clearly shown that the stapled channel 142, guide wire channel 144 and balloon inflation channel 146 may all be stacked on a single vertical axis within the staple housing 114. This orientation constitutes the orientation of the various channels 142, 144, 146 for most of the length of the staple housing 114.

Figure 8:
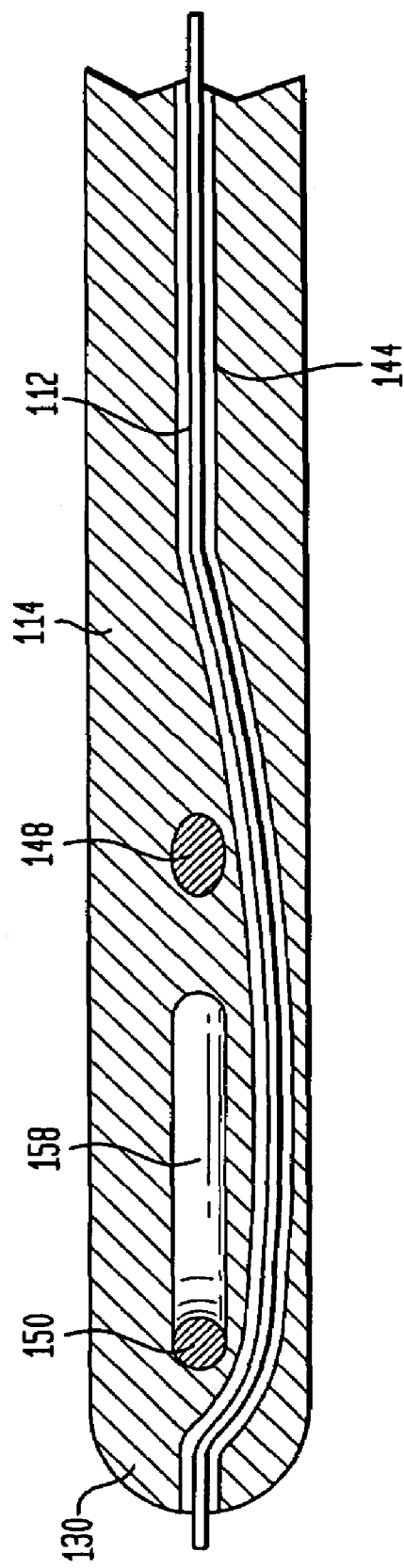
FIG. 8 is a longitudinal section of the distal end of the staple housing shown in FIG. 4 taken along section lines D-D.

FIG. 8 depicts a longitudinal section view of the distal end 130 of staple housing 114 shown in FIG. 4 taken along section lines D-D. In this view, the staple exit area 158 is clearly depicted with the proximal end 150 of the staple 148 nearest the distal end 130 of the staple housing 114. Also shown in the guide wire channel 144 with the guide wire 112 offset to permit formation of the staple exit area 158.

Figure 9:
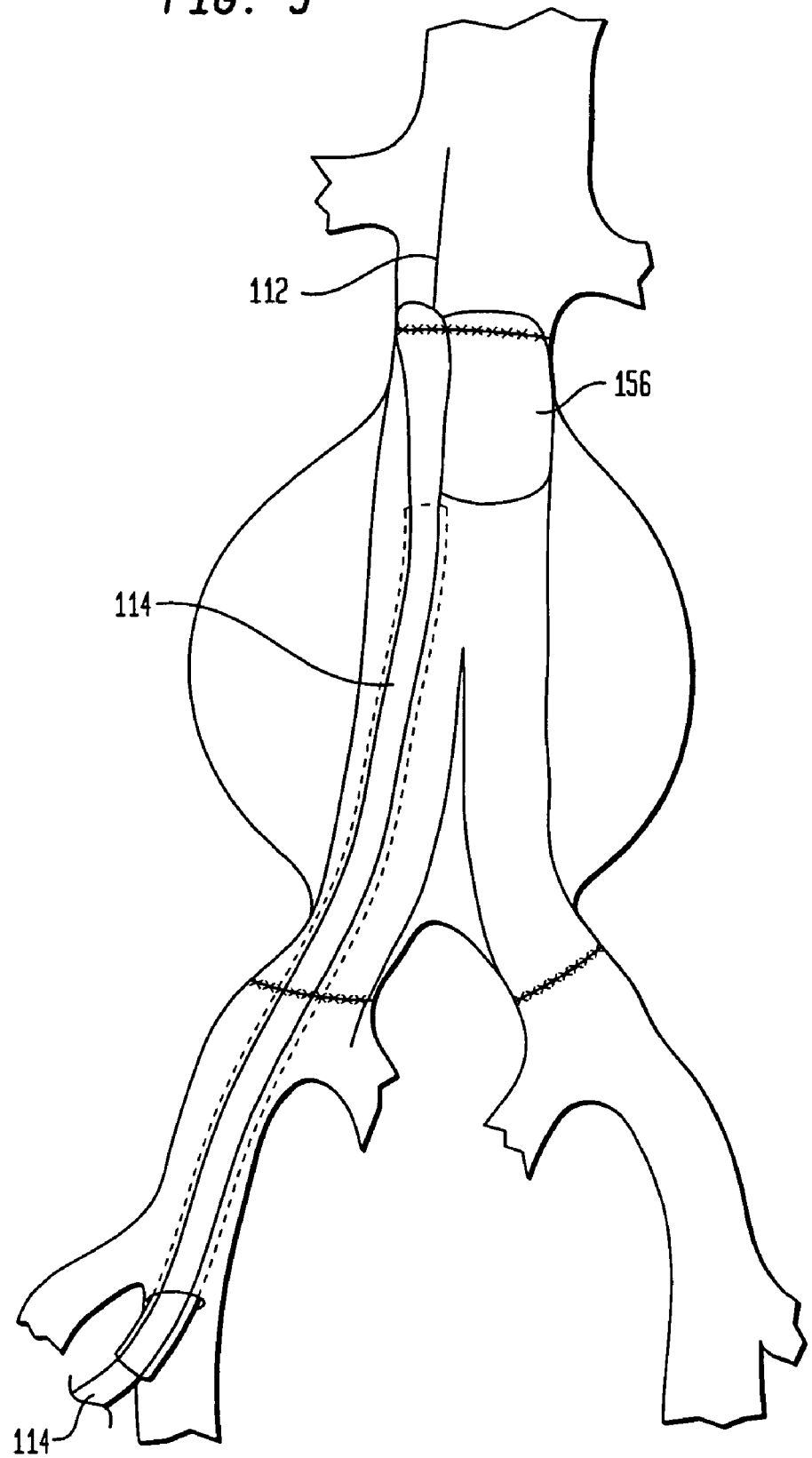
FIG. 9 is a cut-away view of the abdominal cavity of a patient depicting the general orientation of the staple housing forming a portion of the stapler utilized in a method of arresting graft migration in accordance with one embodiment of the present invention.

FIG. 9 depicts a staple housing 114 inserted into a sheath within the human body. The staple housing 114 is typically introduced into the groin or other suitable access area where it follows the previously inserted guide wire 112 into the lumen of the endograft to be sutured. Also shown in FIG. 9 is the noncompliant balloon 156 in a fully inflated condition. As previously discussed, the distal end 130 of the staple housing 114 will be pushed against the aortic sidewall by the noncompliant balloon 156. When so pushed, a first staple 148a may be fired. Subsequent staples 148 may be fired after deflation of the noncompliant balloon 156, rotation of the staple housing 114 and inflation of the noncompliant balloon such that the staple exit area 158 is aligned at the intended deployment location.

Figure 10:
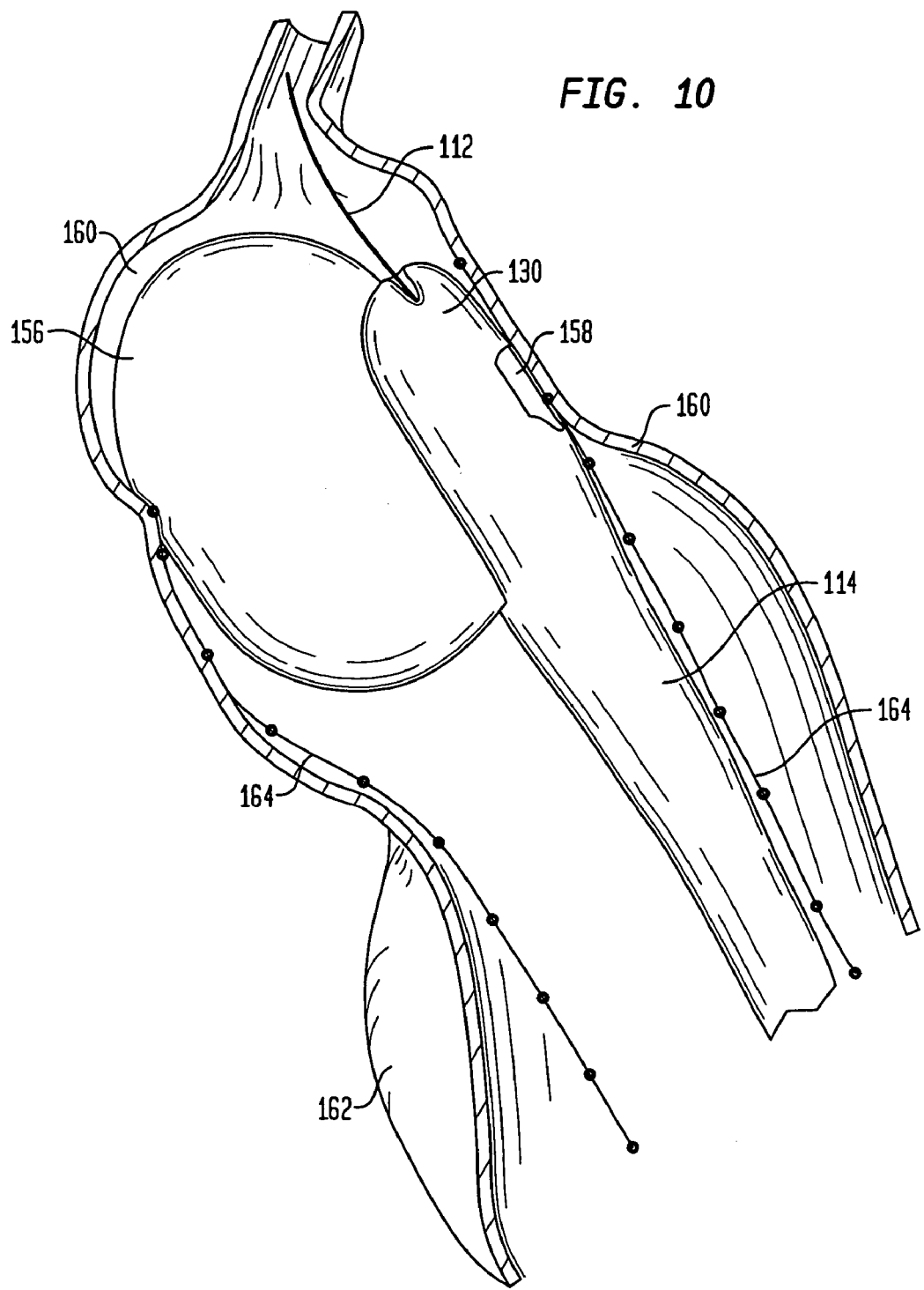
FIG. 10 is a second cut-away view of the abdominal cavity of a patient depicting the general orientation of the staple housing forming a portion of the stapler utilized in the method of arresting graft migration in accordance with one embodiment of the present invention.

FIG. 10 depicts a close-up cut-away view of the distal end 130 of the endovascular stapler 100 in use. As discussed, the distal end 130 of the stapler 100 may be inserted into the aorta 160 through a sheath (not shown) along a guide wire 112. The proximal end 130 may then be positioned so as to cover the aortic aneurysm 162 intended to be cured. As previously discussed, the noncompliant balloon 156 may then be enlarged such that the staple exit area 158 of the stapler 100 will be pushed up against the endograft 164 and the aortic sidewall 160, as shown in FIG. 10.

Figure 11:
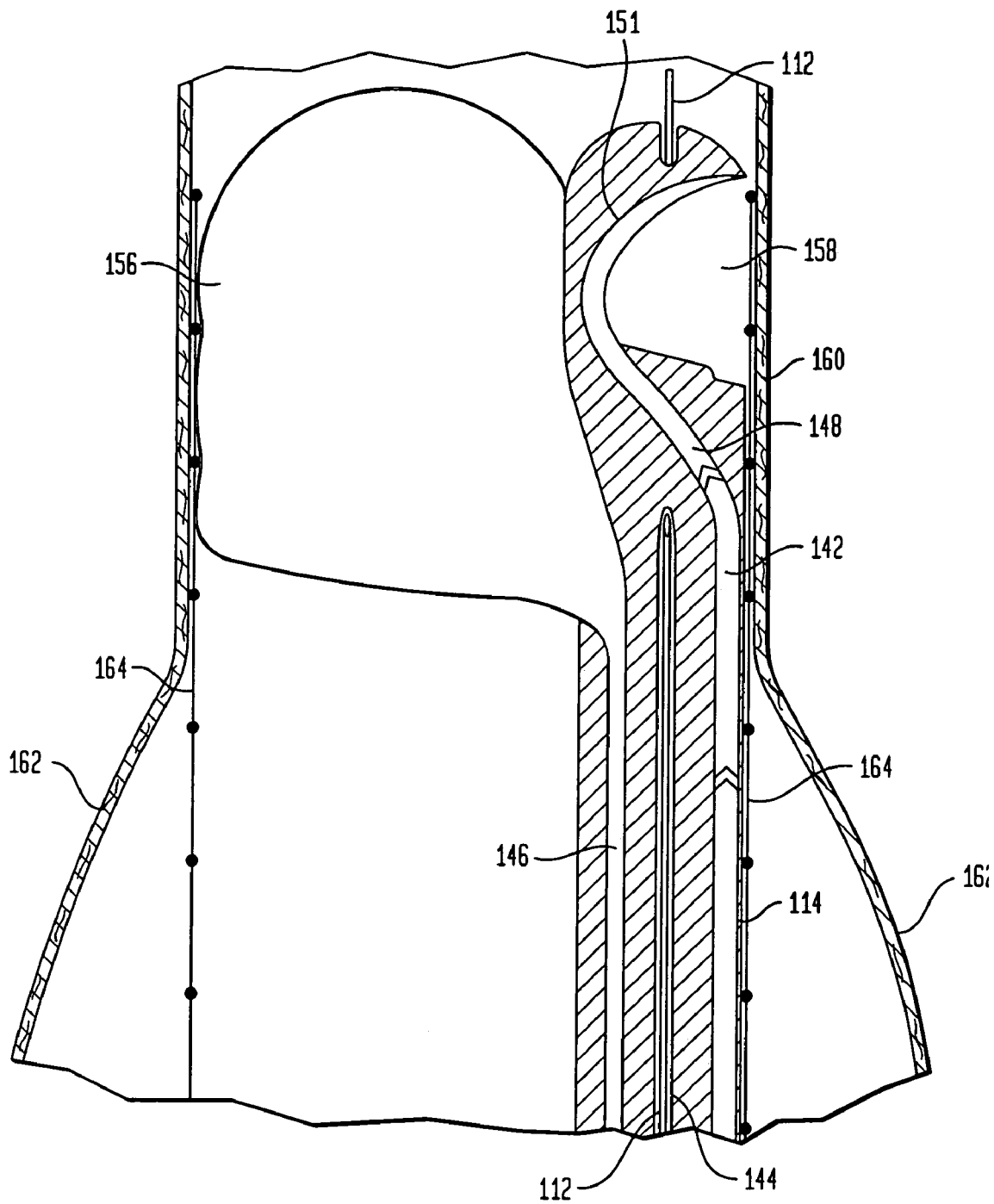
FIG. 11 is a cut-away view of the abdominal cavity of a patient depicting an initial step of the method of affixing a graft into an aortic aneurysm in accordance with one embodiment of the present invention.

FIG. 11 depicts a longitudinal section view of this arrangement showing the internal components of the staple housing 114. In this view, it is clearly shown that the first staple 148a is being pushed by the second staple 148b through the curved area 153 of the staple channel 142. Such curvature of the staple channel deforms the first staple 148a permitting the staple to curve around the curved internal staple guide 151 toward the staple exit area 158. Again, the staple exit area 158 is shown adjacent to the area in which the staple 148 is to be deployed. Secure placement of the staple exit area 158 is achieved via inflation of the noncompliant balloon 156.

Figure 12:
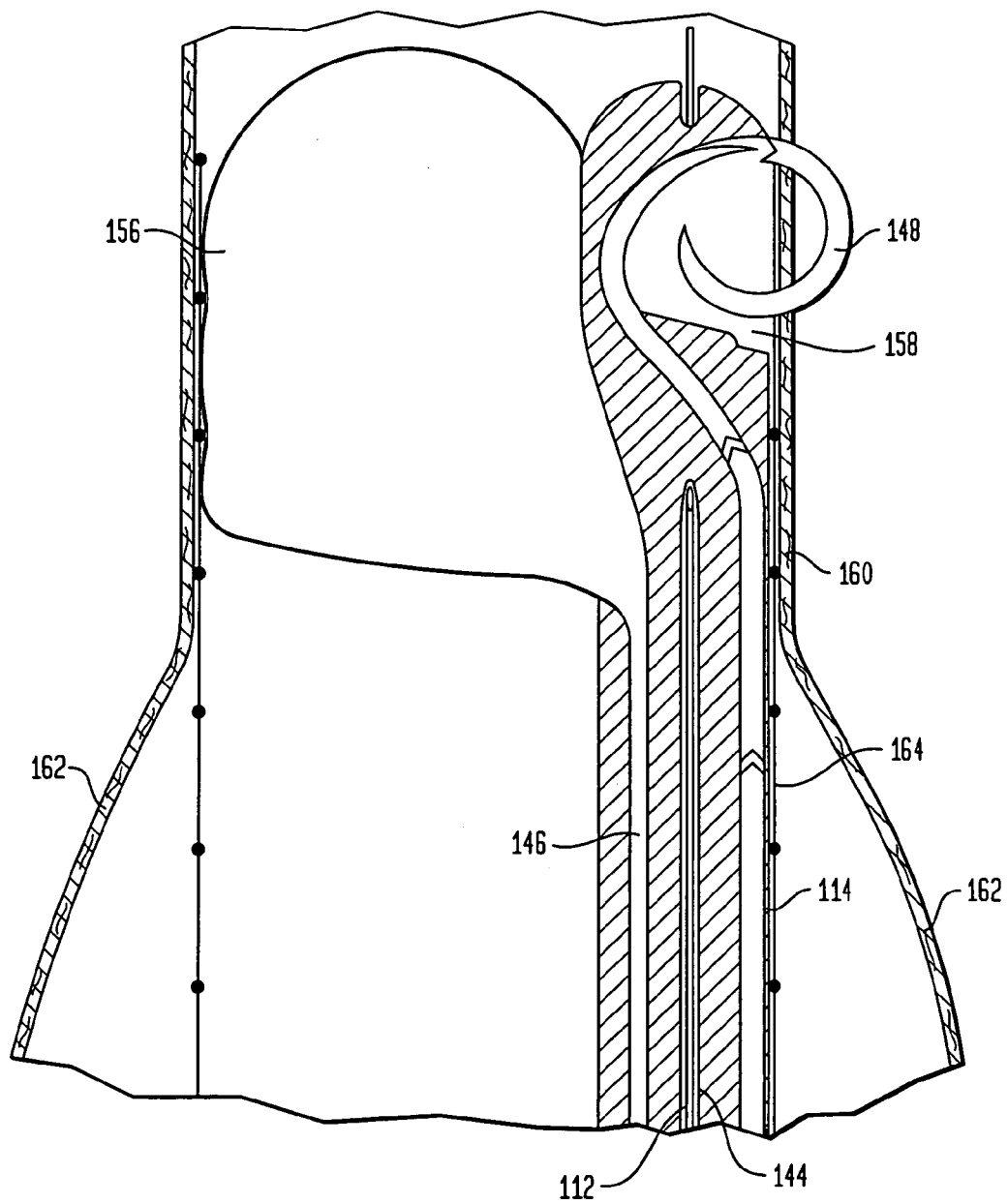
FIG. 12 is a cut-away view of the abdominal cavity of a patient depicting a further step of the method of affixing a graft into an aortic aneurysm of FIG. 11.

FIG. 12 depicts the longitudinal section view of FIG. 11 after the firing of a staple 148. As shown, internal staple guide 151 has formed the staple 148 into a ring or loop engaging the endograft 164 and the aortic sidewall 160 from the interior of the aorta 160 and then returning back around to again engage the aortic sidewall 160 and the endograft 164 from the exterior of the aorta. As previously discussed, the noncompliant balloon 156 may then be temporarily deflated such that the staple housing 114 may be rotated and placed in a position for the firing of a second staple 148b.

The stapler is typically introduced into the patient through a groin sheath or other suitable access into the lumen of the endograft. It is advanced to the proximal end of the endograft which should be accurately identified. For future endografts, the ends of the graft fabric is boldly marked with radio opaque thread. For older devices, radiologic techniques such as road mapping may be used to locate the ends of the graft. As is known in the art, multiple guide wires may be used during surgery.

When the stapling end of the stapler is aligned with the end of the endograft, the stapler head is forcibly abutted against the endograft and vessel wall by inflation of a balloon. In this position, pulling of the stapler trigger causes forward displacement of the staple pusher sufficient to advance a single staple through the graft and vessel wall. The curve of the staple guide causes the staple to form a circle. The trigger of the stapler handle is then cocked for the next firing. The specialized ratcheted design of this pusher and trigger is such that when fully cocked, the trigger pull causes exactly the pusher excursion needed to deploy the lead staple fully and bring the trailing staple segment into position at the tip of the curved staple guide.

Inflation of the preferably noncompliant balloon may be performed manually or with any of the many available devices used for inflation of angioplasty balloons. A liquid such as dilute contrast or saline may be used to distend the balloon.

Following each staple deployment, the balloon is deflated, the stapler is rotated and the process is repeated to deploy the next staple. The only limiting factor to the number of staples per device, and thus the length of the device, is the column strength of the staple alloy as the staples aligned in a row are driven each by the trailing staple and ultimately by the excursion of the staple pusher.

The staples are cut such that the diamond shaped tip of the trailing staple fits into the diamond shaped cavity formed at the end of the lead staple.

Figure 14:
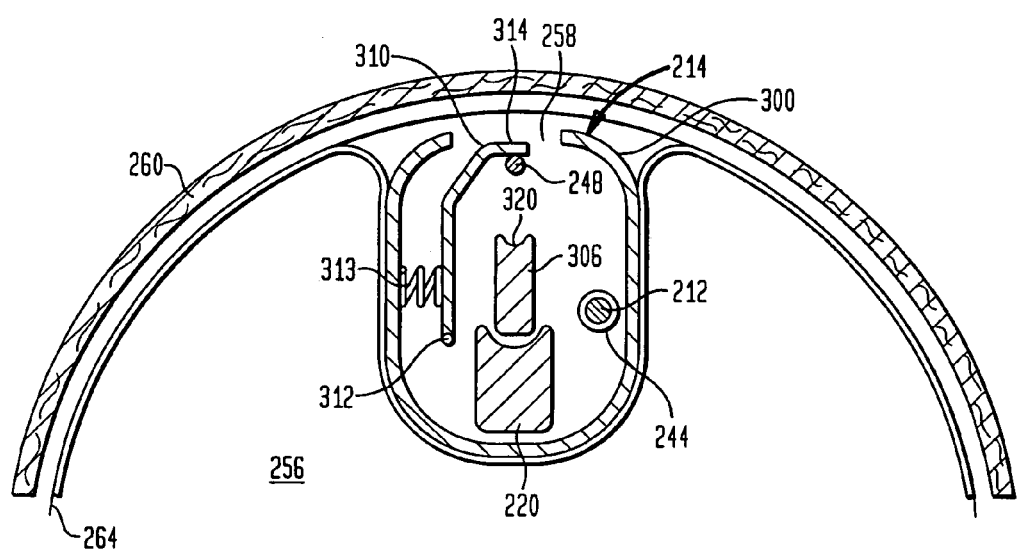
FIG. 14 depicts a cross-sectional view of the distal end of the staple housing of the stapler in accordance with the second embodiment of the present invention in an initial position.

FIG. 14 depicts a cross-sectional view of a portion of the staple housing 214 of an endovascular stapler (not shown) in accordance with a second embodiment of the present invention. In this embodiment, a single staple 248, formed in the shape of an elongated W may be applied to secure a graft 264 against a vessel, shown in FIG. 14 as an aortic wall 260. Typically, the chief function of a stapler in accordance with this embodiment is for use to arrest device migration of a previously placed endograft. Other embodiments employing multiple elongated W-shaped staples may also be used to arrest device migration of a previously implanted endograft or to affix a new endograft. Still further embodiments permit the withdrawal of portions of the stapler which may then be replaced with other portions pre-loaded with a staple for a subsequent firing.

Figure 13:
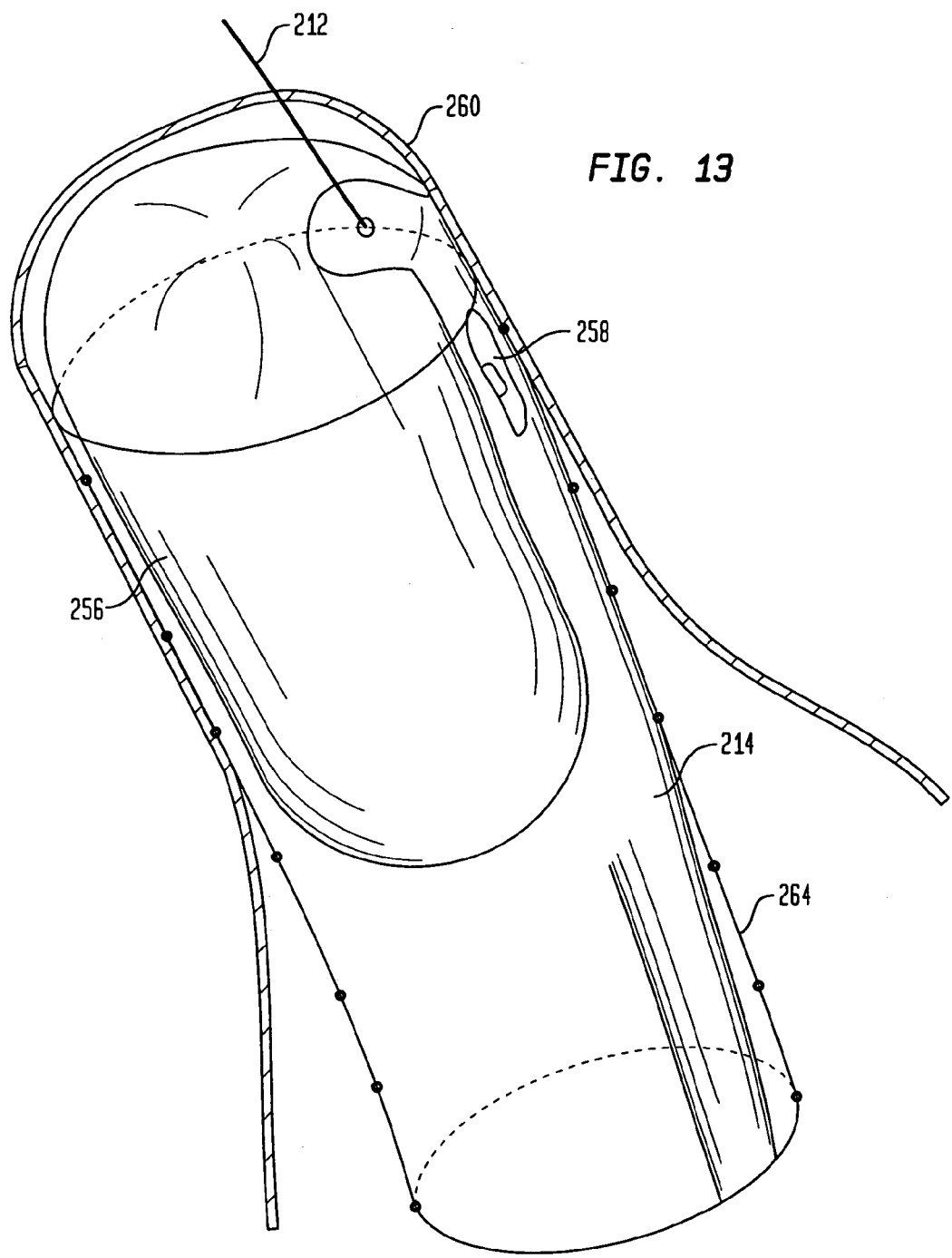
FIG. 13 is a sectional view of a portion of an endovascular stapler in accordance with a second embodiment of the present invention inserted into an aortic wall.

FIG. 13 depicts a partially cut-away perspective view of a stapler housing 214 and a noncompliant balloon 256 inserted within an aortic wall 260 in preparation for attachment of a stent graft 264. As shown in FIG. 13, the stapler housing 214 may be placed into position by being strung along a guide wire 212 in an "over the wire" type system, as previously discussed. Once positioned properly, such that the staple exit area 258 is adjacent to the intended deployment area, the noncompliant balloon 256 may be inflated, as shown in FIG. 13, to push the staple exit area against the stent graft 264, which in turn is pushed against the aortic wall 260. The staple 248 may then be fired and the stapler housing 214 removed.

Firing of the staple 248 may be achieved utilizing a housing with a ratcheted trigger, as with other embodiments of the invention.

Figure 15:
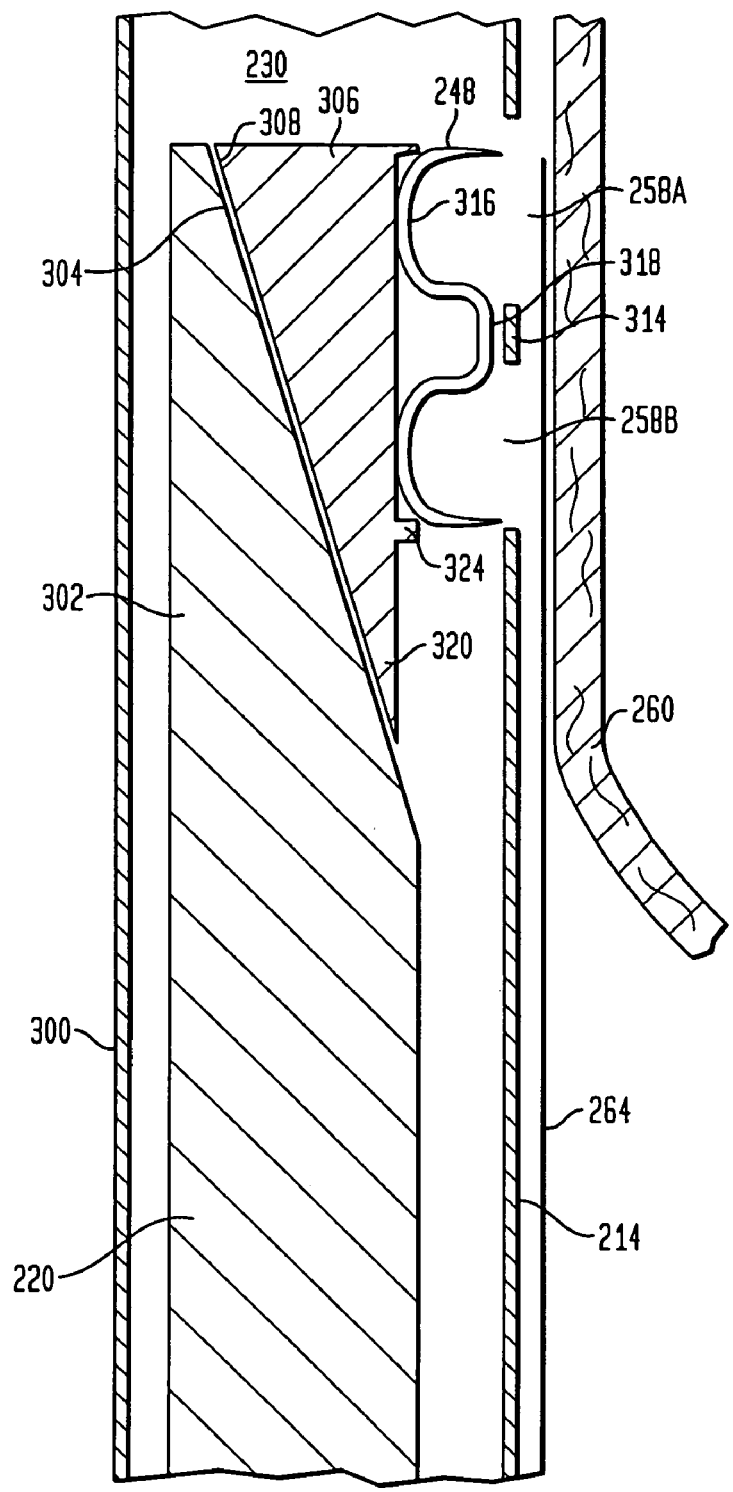
FIG. 15 depicts a longitudinal section view of the distal end of the staple housing of the stapler in accordance with the second embodiment of the present invention in the initial position shown in FIG. 14.

As shown in FIG. 14, the staple housing 214 may include an exterior casing 300 having a staple exit area 258 at its distal end 230 (FIG. 15). A pusher 220 may extend the full length of the exterior casing 300, from stapler to the staple exit area 258. As shown in FIG. 15, the pusher 220 includes a tapered section 302 adjacent the staple exit area 258. The tapered section 302 includes an inclined surface 304. Adjacent the inclined surface 304 is an actuator 306. The actuator 306 includes an inclined surface 308 adjacent the inclined surface 304 of the tapered section 302.

Referring back to FIG. 14, there is shown a staple détente 310 shown within the exterior casing 300. Although not shown in the figures, the stapler détente 310 is connected at one end to the exterior housing 300 by a rotatable connection, such as a hinge 312 mounted to the housing or to protruding portions of the housing. Two such protruding portions may also support a rod about which the détente 310 may be rotated and to which the détente 310 may be connected. The rod may span the protruding portions or may be connected to them at internal intervals of the rod.

The second end 314 of the staple détente 310 may extend toward the staple exit area 258, to divide the staple exit area into a first staple exit area 258A and a second staple exit area 258B, as shown in FIG. 15. A spring 313 may be mounted between the exterior casing 300 and the staple détente 310 such that the détente is biased into the position shown in FIG. 14, where the spring is shown in its fully extended position. As will be discussed, the détente 310 may be rotated from this position upon application of a compressive force upon the spring 313.

As with the first embodiment, a guide wire channel 244 is also located within the staple housing 214. The guide wire channel 244 permits the use of a guide wire 212 in an "over the wire" system, to properly place the staple exit area 258.

FIG. 14 also depicts a portion of a noncompliant balloon 256. The noncompliant balloon 256 of the second embodiment may be completely exterior of the staple housing 214. The noncompliant balloon 256 is intended to be inflated such that the staple housing 214 will be pushed against the stent graft 264 such that the stent graft may be firmly apposed against the aortic wall 260.

Also included within the staple housing 214 is an elongated W-shaped staple 248. As shown in FIG. 15, the staple 248 includes two U-shaped sections 316 connected by a bridge 318. Each of the U-shaped sections 316 of the staple 248 sits against the front surface 320 of the actuator 306. At the extreme ends of the staple 248, the front surface 320 extends out to form flanges 324 which act to capture the staple and secure it in place. In addition, the front surface 320 of the actuator is curved, as shown in FIG. 14, to assist with securing the staple 248 in place.

Figure 16:
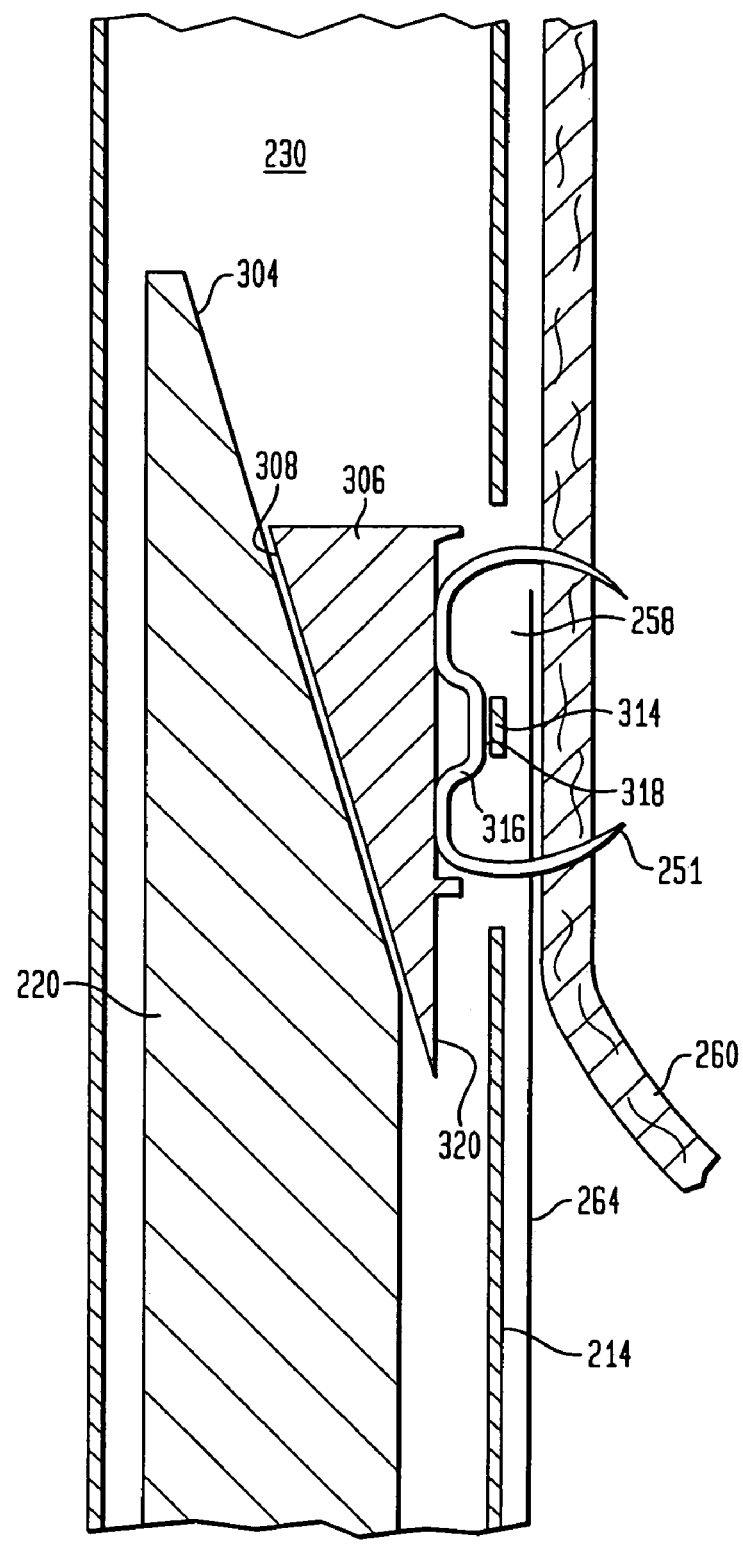
FIG. 16 depicts a longitudinal section view of the distal end of the staple housing of the stapler in accordance with the second embodiment of the present invention in an advanced position.
Figure 17:
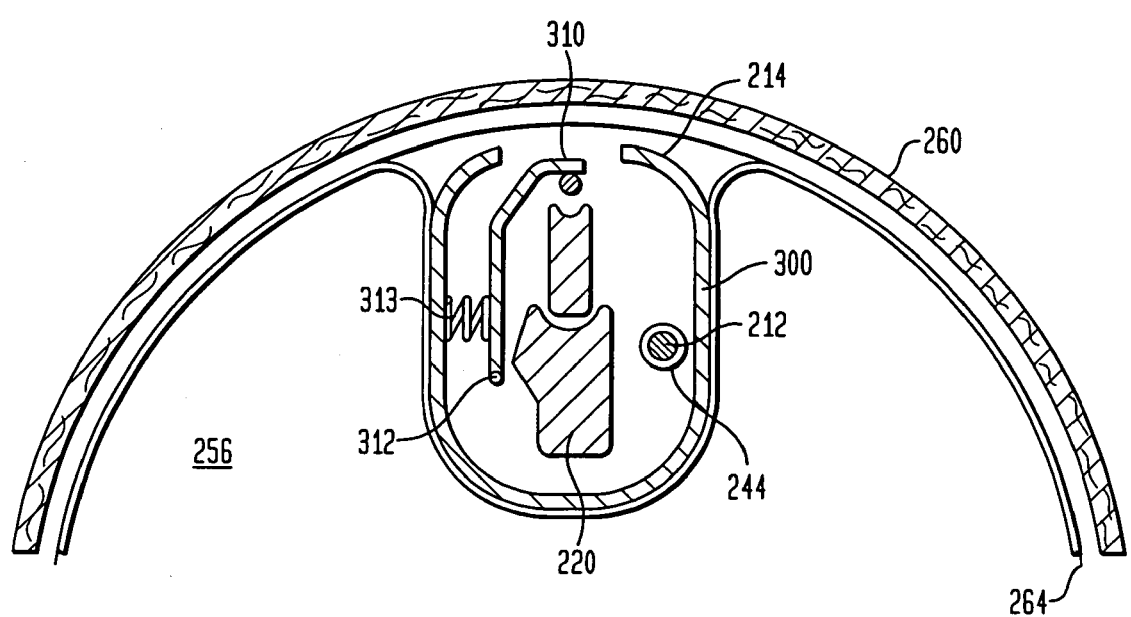
FIG. 17 depicts a cross-sectional view of the distal end of the staple housing of the stapler in accordance with the second embodiment of the present invention in the advanced position shown in FIG. 16.

As the trigger of the stapler is actuated, the ratcheted stapler pusher 220 is advanced toward the distal end 230 of the staple housing 214. As shown in FIG. 16, advancement of the pusher 220 toward the distal end 230 of the staple housing 214 causes the inclined surface 304 of the pusher to contact the inclined surface 308 of the actuator 306. As the pusher 220 is advanced, the front surface 320 of the actuator 306 will be pushed perpendicularly toward the staple exit area 258 due to the interaction between the inclined surfaces 304, 308. Advancement of the actuator 306 will push the bridge 318 of the staple 248 against the second end 314 of the staple détente 310, as shown in FIGS. 16 and 17. This advancement causes portions of the U-shaped sections 316 of the staple 248 to flatten along the axis of the bridge 318 and front surface 320 of the actuator 306. Other portions of the U-shaped sections 316 extend from within the staple housing 214 such that the pointed ends 251 of the staple may penetrate the endograft 264 and the aortic wall 260.

Figure 20:
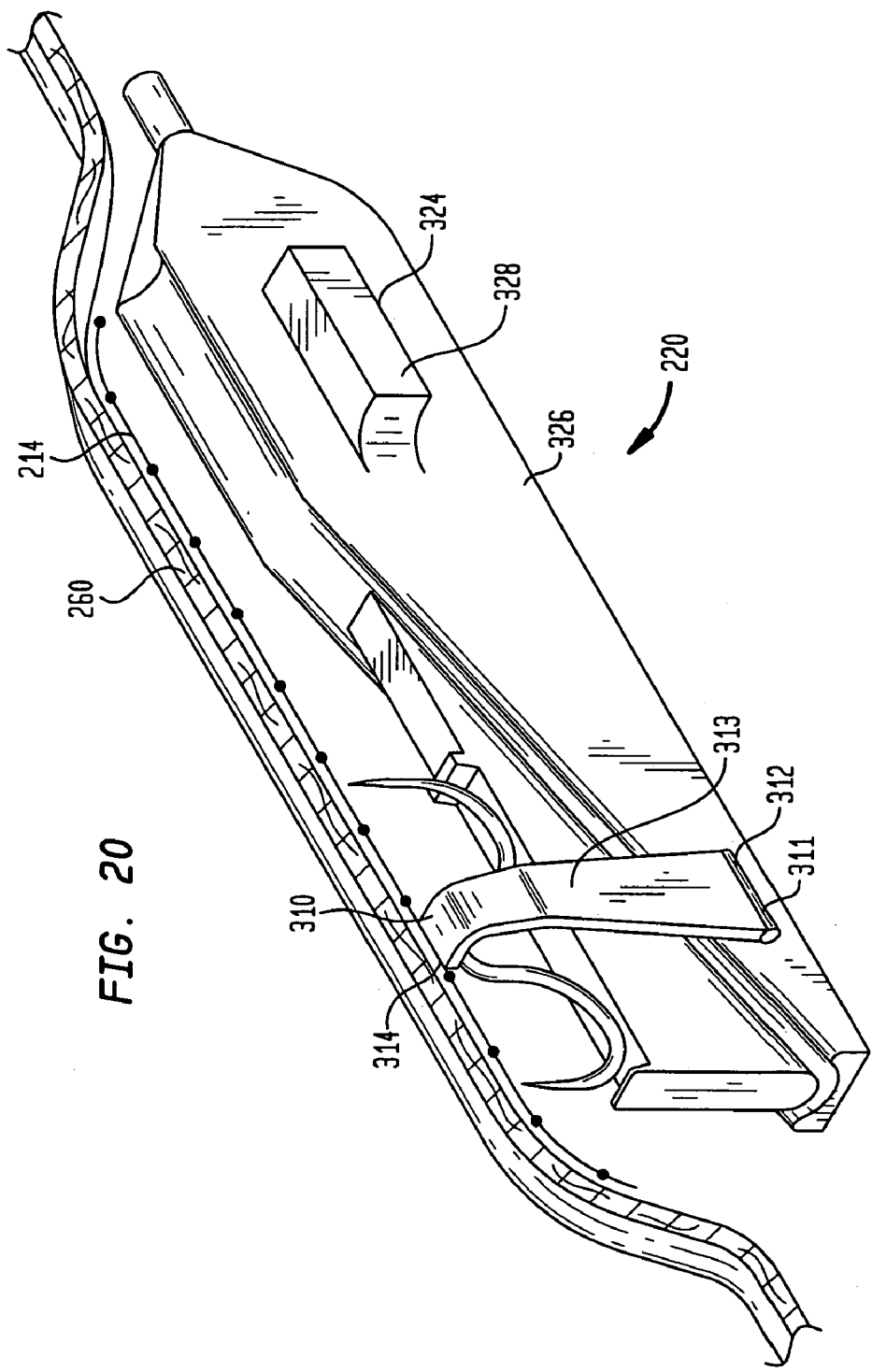
FIG. 20 depicts a perspective view of several internal components forming a portion of the stapler in accordance with the second embodiment of the present invention.

Referring briefly to FIG. 20, the pusher 220, in accordance with the second embodiment of the present invention, is shown with an elevated portion 324 on its side 326. The elevated portion 324 includes a transition area 328 ramping down toward the flat surface of the side 326 of the pusher 220. As the pusher 220 is displaced, the elevated portion 324 moves toward the middle portion 313 of the staple détente 310. Once the transition area 328 comes in contact with the middle portion 313 of the staple détente 310, the staple détente will be rotated about its first end 311 at hinge 312 to compress the spring 313 such that its second end 314 is no longer in contact with the staple 248.

Figure 19:
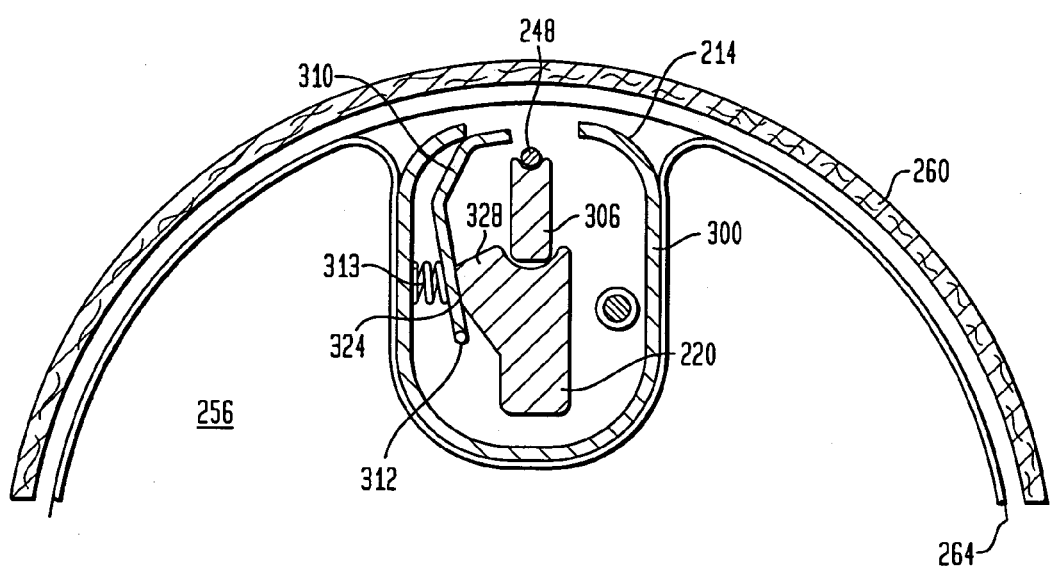
FIG. 19 depicts a cross-sectional view of the distal end of the staple housing of the stapler in accordance with the second embodiment of the present invention in the further advanced position of FIG. 18.

FIG. 19 depicts a cross-sectional view of a portion of the staple housing 214 of an endovascular stapler where the pusher 220 has been advanced such that the elevated portion 324 is in contact with the staple détente 310. It will be appreciated that advance of the pusher 220 and deflection of the staple détente 310 is conducted against the biasing force of the spring 313.

Figure 18:
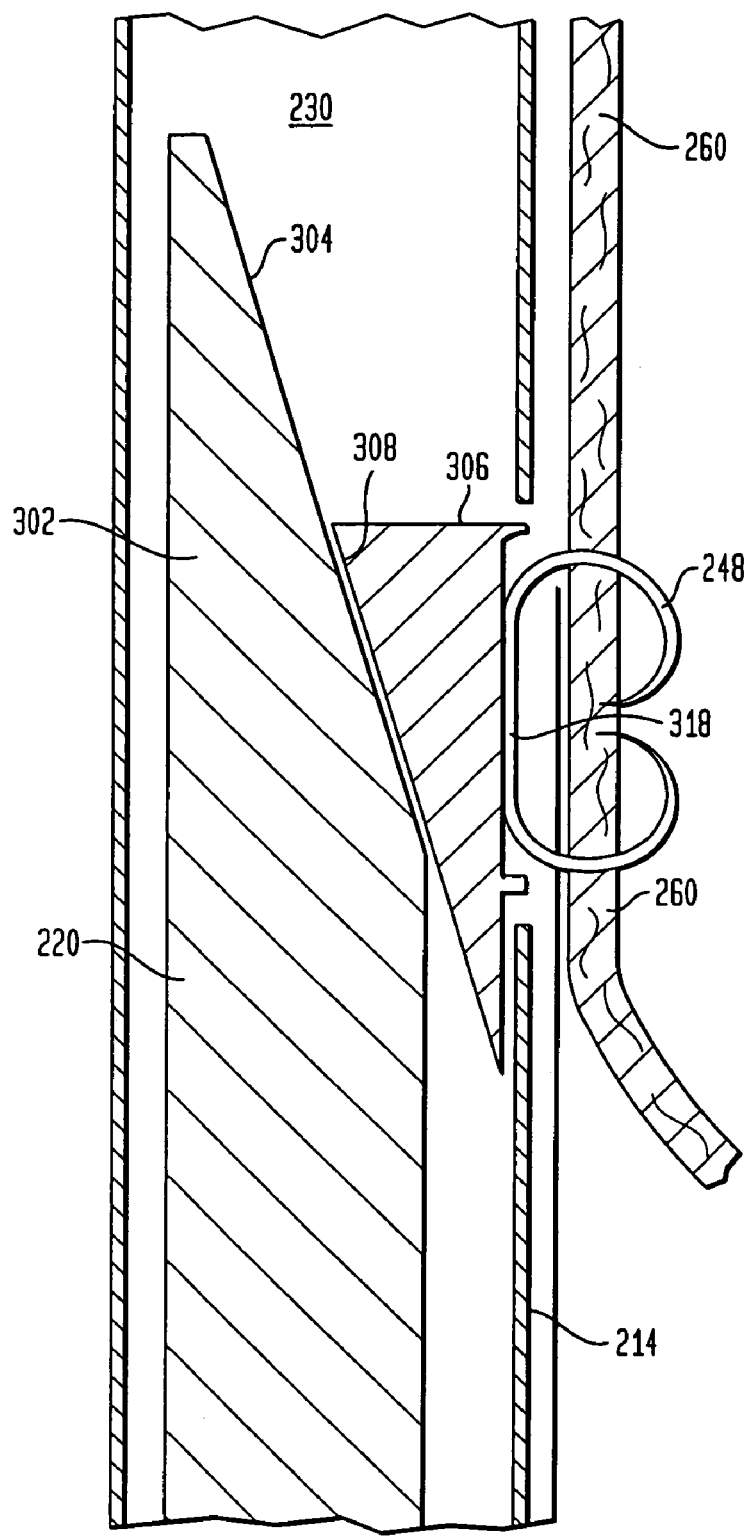
FIG. 18 depicts a longitudinal section view of the distal end of the staple housing of the stapler in accordance with the second embodiment of the present invention in an further advanced position.

FIG. 18 depicts a pusher 220 in its fully advanced position such that the staple détente 310 is no longer in contact with the staple 248. As shown in FIG. 18, it will be appreciated that prior to the staple détente 310 being rotated away from the staple 248, the U-shaped sections 316 of the staple 248 will have curved around such that the pointed ends 251 of the staple extend back into the aortic wall 260, and the bridge 318 is extended to include portions of the U-shaped sections, thus forming a closed staple.

The endovascular stapler disclosed with respect to the second embodiment of the present invention is intended to fire a single staple 248. As disclosed, if a subsequent staple 248 was required, the entire staple housing 214, possibly including the noncompliant balloon 256, would be removed from within the body so a second staple may be loaded. Once loaded, the staple housing 214 and, if necessary, the noncompliant balloon 256 may then be reinserted into the body such that a second staple 248 may be fired. This procedure may be repeated as necessary to arrest the migration of the endovascular graft or fully affix a new graft. Rather than reloading the endovascular stapler, a surgeon may choose to be provided with a plurality of endovascular staplers such that each may be utilized in succession without having to be reloaded. It will be appreciated that provision of numerous endovascular staplers saves time in the operating arena, where the duration of an operation is preferably minimized.

Figure 21:
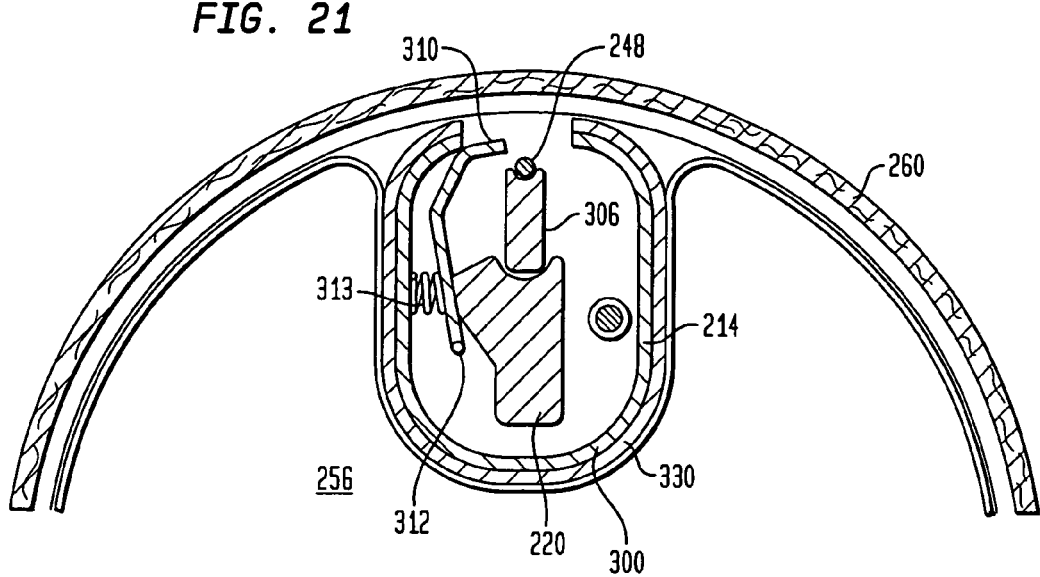
FIG. 21 depicts a cross-sectional view of the distal end of the stapler of the present invention in accordance with a third embodiment; and, FIGS. 22a and 22b depict a triangular apparatus forming a portion of the staple housing which may be utilized in accordance with certain embodiments of the present invention, FIG. 22b depicting the triangular apparatus in a parallel relation and FIG. 22a depicting the triangular apparatus in an angled relation.

In a further embodiment, depicted in FIG. 21, a housing 330 may be disposed between the staple housing 214 and the noncompliant balloon 256. Such a housing 330 permits withdrawal of the staple housing 214, while leaving a cavity within the housing 330 wherein the staple housing may be returned after being reloaded with a subsequent staple (or where the housing of the second or subsequent stapler, may be inserted). The noncompliant balloon 256 may then be partially deflated to permit the staple exit area 258 to be rotated to a subsequent position for the firing of a subsequent staple 248. In this regard, additional staples 248 beyond the initial staple may be inserted in a relatively quick manner, as compared to other embodiments where the noncompliant balloon 258 may be removed and reinserted.

In further embodiments, additional staples may be mounted on a cartridge within the staple housing 214 to permit the automatic reloading of the device with additional staples. If so provided, a mechanism is included within the housing of the stapler to override the ratcheting function of the stapler trigger, such that the pusher may be retracted to the position shown in FIG. 15 from the position shown in FIG. 18. Once retracted into the position shown in FIG. 15, it is anticipated that a spring loaded stapler feed mechanism may reload the actuator with an additional staple automatically. Preferably, the automatic loading device would be capable of feeding up to seven staples, such that a total of eight staples may be fired without removal of the staple housing. It will be appreciated that eight staples are generally sufficient to connect the graft to a vessel. Of course, a loading device capable of supplying a greater number of staples may also be provided.

In further embodiments, multiple staples may be fired simultaneously from a single staple housing 214. In such embodiments, the staple housing 214 may include multiple staples 316 arranged radially about a centerline of the staple housing. The staples 316 may also be side-by-side in a linear relationship. Each of the staples 316 may be deployed simultaneously through interaction of the pusher 220 and the actuator 306. In such embodiments, the staple housing 214 preferably includes a staple détente 310 for each staple to be deployed. For example, in one embodiment employing two staples 316, a staple détente 310 may be mounted on each side of the pusher 220 by separate hinges 312. Each of the détentes 310 may be on opposite sides of the pusher 220, such that they can freely rotate without interfering with each other.

Figure 22A:
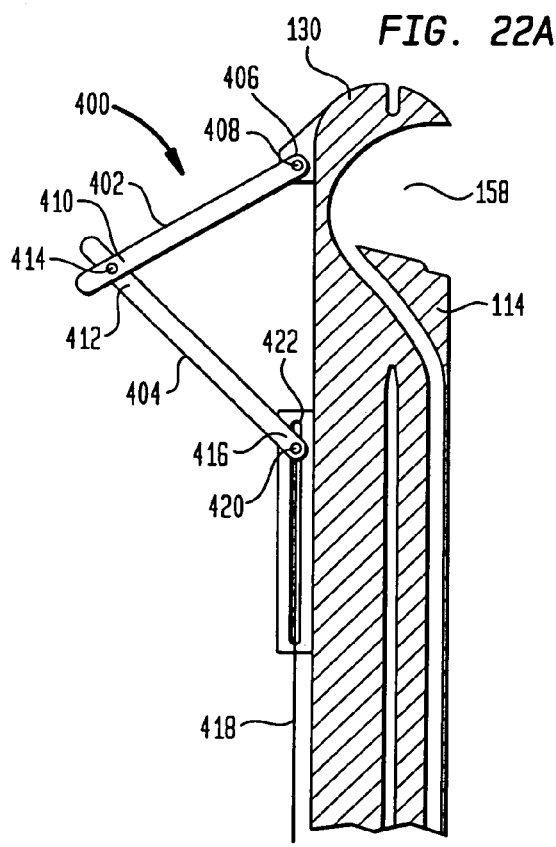
Figure 22B:
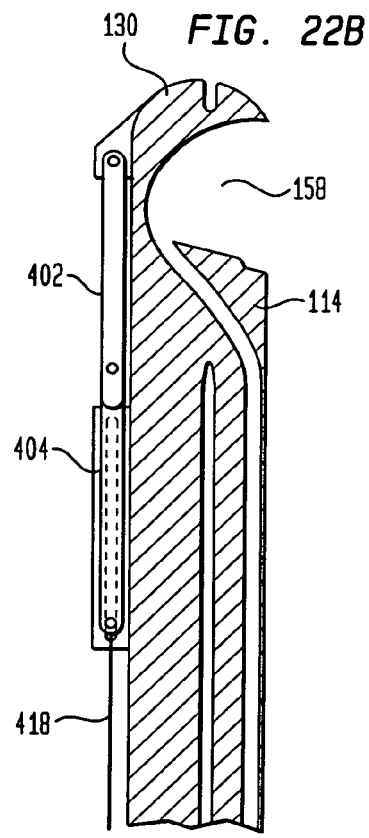

In addition to utilizing a balloon, such as the noncompliant balloon, to abut the staple exit area of the staple housing against the vessel wall or graft, other means may be employed. For example, as shown in FIGS. 22a and 22b, a simple triangular shaped apparatus 400 may be utilized. The apparatus 400 may comprise two elongate rods 402, 404. The first end 406 of the first rod 402 may be pivotally attached to the distal end 130 of the staple housing 114 by a pin 408. The second end 410 of the first rod 402 may be pivotally attached to the first end 412 of the second rod 404 by a pin 414. Finally, the second end 416 of the second rod 404 may be slideingly engaged to the staple housing 114 This sliding engagement may be achieved by utilizing a pin 420 slideable within a groove 422 created in the staple housing. A handle 418 may extend the length of the staple housing 114 to the housing 102 of the stapler 100.

Typically, if the rods 402, 404 are parallel to the longitudinal axis of the staple housing, such as shown in FIG. 22b, they will be adjacent to the staple housing 114, tight against its exterior wall. If the handle 418 is pushed forward toward the distal end 130 of the stapler 100, it will be appreciated that the pivot point between the first rod 402 and the second rod 404, located at pin 414, will be forced to extend from the exterior wall of the staple housing 114, as shown in FIG. 22a. If that pivot point 414 contacts the inner wall of a vessel, it will force the opposite side of the staple housing to move away from the portion of the inner wall contacting the pivot portion. Thus, the apparatus may be mounted opposite the staple exit 158 area to appose the staple exit area against the vessel wall in a predetermined area. Of course, multiple such triangular apparatuses, or parallelograms of greater than three sides comprising additional components, may also be utilized. In certain applications this type of displacement device may be preferred as it will not completely block or occlude the vessel, such that blood flow may continue.

In addition, although not shown, it will be appreciated that in other embodiments, the handle 418 may be positioned within a channel extending through the interior of the staple housing, similar to the balloon inflation channel previously discussed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In this regard, elements such as the trigger have been described in a particular manner. It is to be understood that the trigger mechanism and others like it, may be manufactured differently. For example, in lieu of a trigger, a simple dial advancement mechanism may be utilized to displace the pusher within the stapler cavity. If so provided, the gear ratio of the dial may be designed such that a given number of turns of the dial will advance the staple pusher a distance coordinated with the length of a single staple.

The invention claimed is:

1. A stapler for stapling a vessel comprising:
    a trigger housing having an internal cavity;
    a trigger mechanism extending from within said internal cavity of said trigger housing;
    an elongate staple housing extending from said trigger housing to a staple exit area formed in said elongate staple housing, said elongate staple housing adapted to store at least one staple;
    a pusher having a leading portion within said staple housing and a trailing portion within said internal cavity of said trigger housing, said pusher having an inclined surface at its leading end;
    an actuator having an inclined surface disposed adjacent to said inclined surface of said pusher;
    a staple détente mounted within said staple housing between said actuator and said staple exit area;
    wherein actuation of said trigger advances said leading portion of said pusher such that said inclined surface of said pusher interacts with said inclined surface of said actuator to force said actuator toward said staple exit area thereby deforming said at least one staple by engagement with said staple détente prior to discharging said at least one staple from said staple exit area.

2. The endovascular stapler of claim 1, wherein said at least one staple stored in said staple housing is formed in the shape of an elongated W prior to being discharged from said staple exit area.

3. The endovascular stapler of claim 1, further comprising a balloon adapted to be expanded adjacent to said staple housing to push the staple exit area of said staple housing against the vessel to be stapled.

* * * * *